(12) United States Patent
    Jeon

(10) Patent No.:     US 12,133,682 B2
(45) Date of Patent:     Nov. 5, 2024

(54) METHOD AND SYSTEM FOR VIRTUAL REALITY-BASED VISUAL FIELD INSPECTION

(71) Applicant: M2S CO., LTD, Seongnam-si (KR)

(72) Inventor: Sang Jin Jeon, Seongnam-Si (KR)

(73) Assignee: M2S CO., LTD, Seongnam-si (KR)

( * ) Notice: Subject to any disclaimer, the term of this patent is extended or adjusted under 35 U.S.C. 154(b) by 695 days.

(21) Appl. No.: 17/273,667

(22) PCT Filed: Jul. 24, 2019

(86) PCT No.: PCT/KR2019/009158
    § 371 (c)(1),
    (2) Date: Mar. 4, 2021

(87) PCT Pub. No.: WO2020/050497
    PCT Pub. Date: Mar. 12, 2020

(65) Prior Publication Data
    US 2021/0315453 A1     Oct. 14, 2021

(30) Foreign Application Priority Data

Sep. 4, 2018  (KR) .................. 10-2018-0105160
Sep. 4, 2018  (KR) .................. 10-2018-0105193
Jan. 15, 2019 (KR) .................. 10-2019-0005151

(51) Int. Cl.
    *A61B 3/10*     (2006.01)
    *A61B 3/00*     (2006.01)
    *A61B 3/024*    (2006.01)
    *A61B 3/06*     (2006.01)
    *A61B 5/16*     (2006.01)
    (Continued)

(52) U.S. Cl.
    CPC ............ *A61B 3/024* (2013.01); *A61B 3/0033* (2013.01); *A61B 3/0041* (2013.01); *A61B 3/0091* (2013.01); *A61B 3/063* (2013.01); *A61B 5/162* (2013.01); *G02B 27/01* (2013.01); *G06F 3/011* (2013.01); *A61B 3/005* (2013.01);
    (Continued)

(58) Field of Classification Search
    CPC ..... A61B 3/024; A61B 3/0033; A61B 3/0041; A61B 3/0091; A61B 3/063; A61B 3/005; A61B 3/10; A61B 3/113; A61B 5/162; G02B 27/01; G06F 3/011; G06F 3/013
    USPC ................. 351/205, 209–211, 237, 239–243
    See application file for complete search history.

(56) References Cited

U.S. PATENT DOCUMENTS

2018/0296084 A1* 10/2018 Kawahara ............. A61B 3/024
2019/0150727 A1*  5/2019 Blaha ..................... G06F 3/012

FOREIGN PATENT DOCUMENTS

CA          3087775 A1 *  8/2019   ............. G06F 3/011
JP       2016193067 A     11/2016
            (Continued)

OTHER PUBLICATIONS

International Search Report of PCT/KR2019/009158, Oct. 30, 2019, English translation.

*Primary Examiner* — Mahidere S Sahle
(74) *Attorney, Agent, or Firm* — Revolution IP, PLLC

(57) ABSTRACT

A method for virtual reality-based visual field inspection according to an embodiment is a method that performs a visual field inspection on a head-mounted display. The method includes: outputting a background including a background image and a focus point image; outputting an indicator on the background; and sensing user input from an examinee according to output of the indicator.

17 Claims, 14 Drawing Sheets

(51) Int. Cl.
*G02B 27/01* (2006.01)
*G06F 3/01* (2006.01)
*A61B 3/113* (2006.01)

(52) U.S. Cl.
CPC ............... *A61B 3/10* (2013.01); *A61B 3/113* (2013.01); *G06F 3/013* (2013.01)

(56) References Cited

FOREIGN PATENT DOCUMENTS

| | | |
|---|---|---|
| JP | 6230086 B2 | 11/2017 |
| KR | 20170048072 A | 5/2017 |
| KR | 20170075962 A | 7/2017 |
| KR | 20180083069 A | 7/2018 |

* cited by examiner

[FIG. 1]
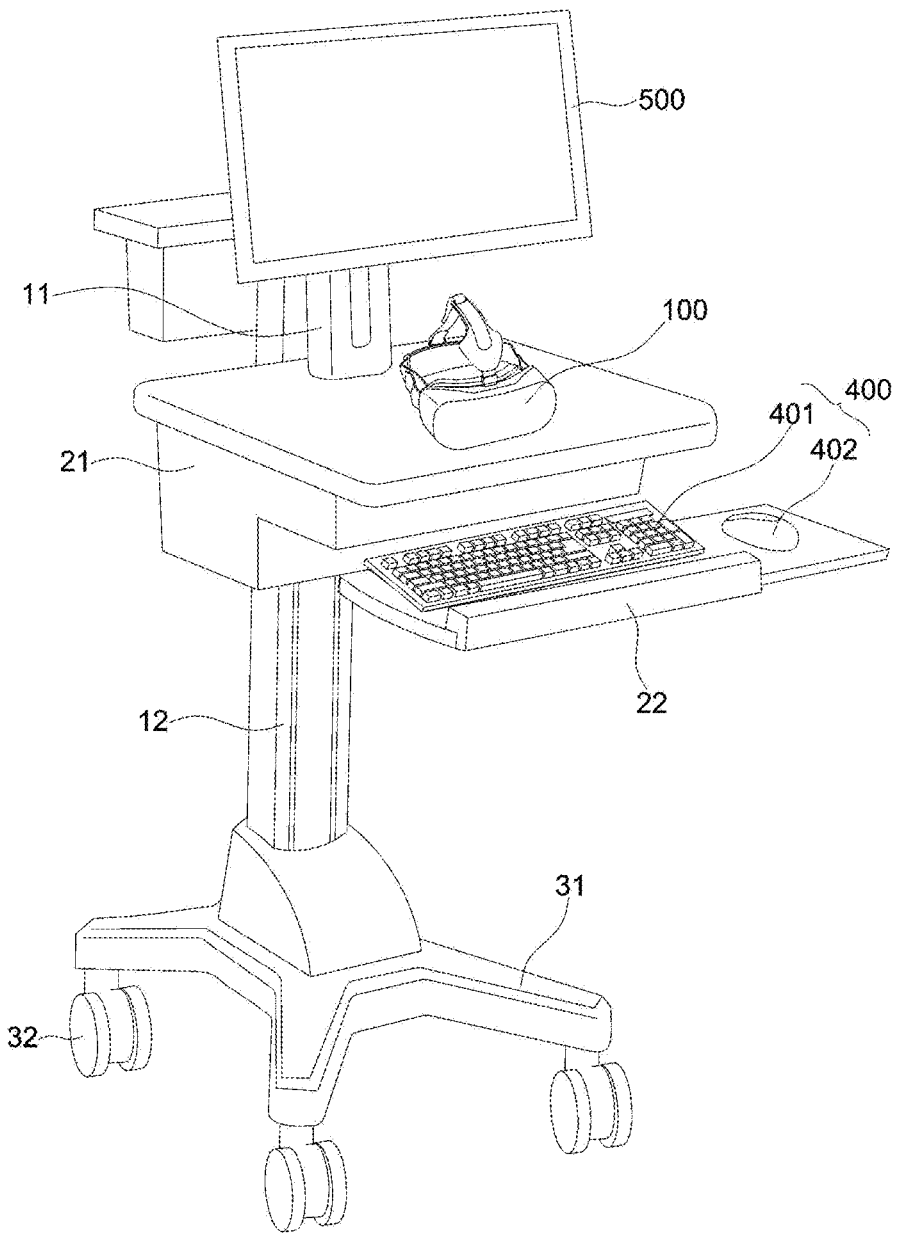

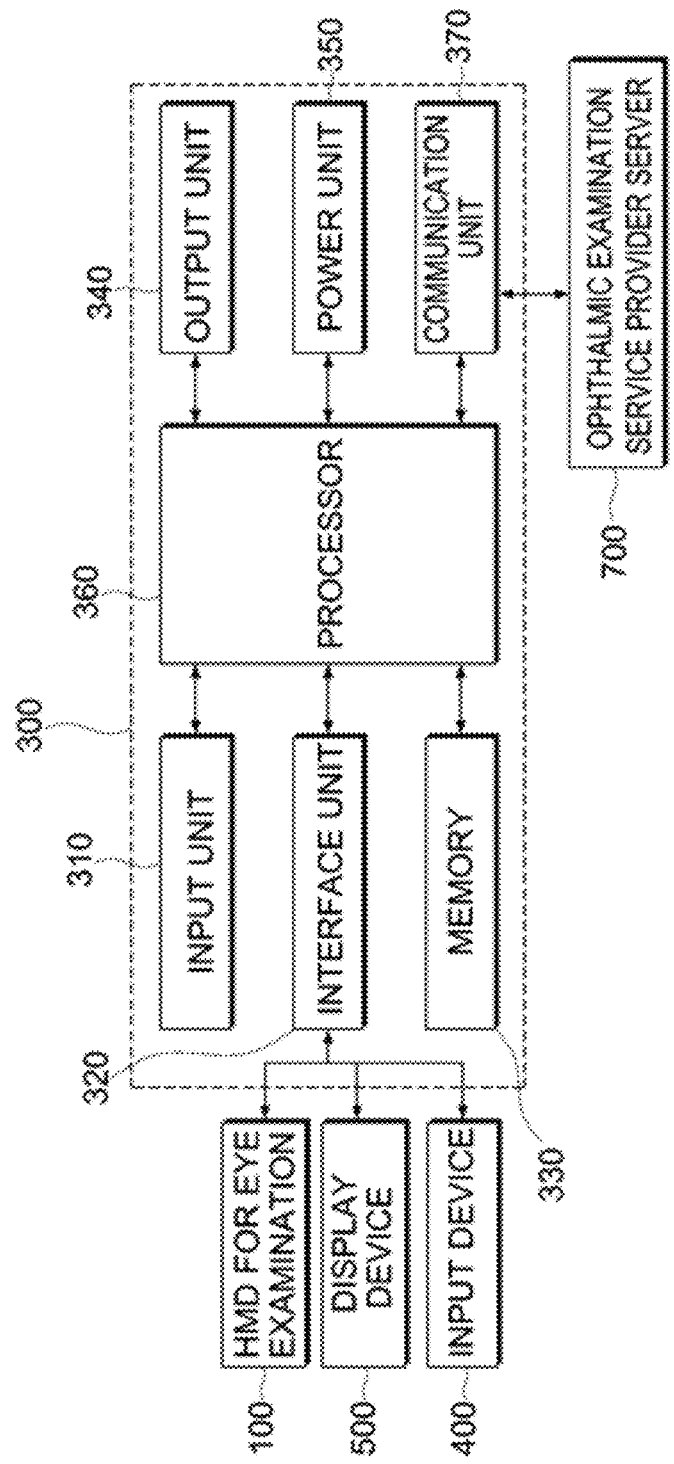
[FIG. 2]

[FIG. 3]
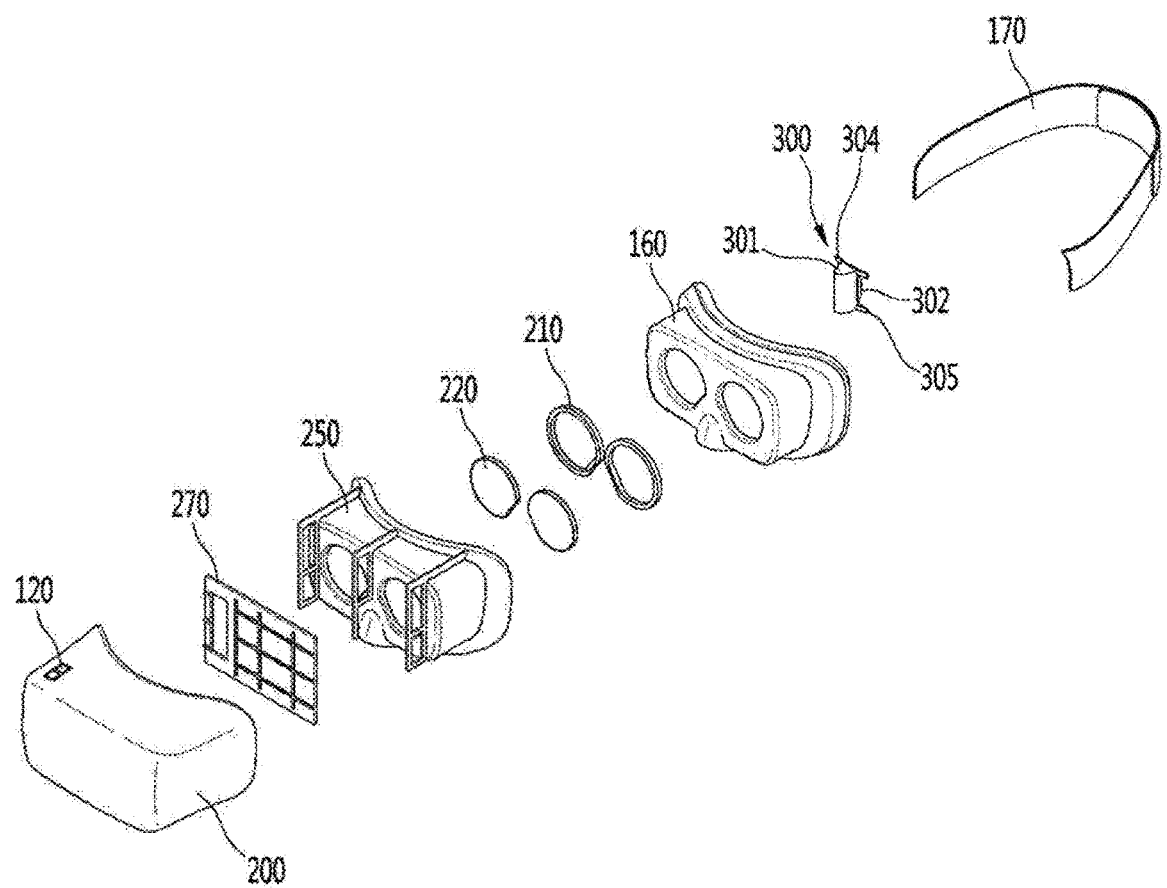
[FIG. 4]
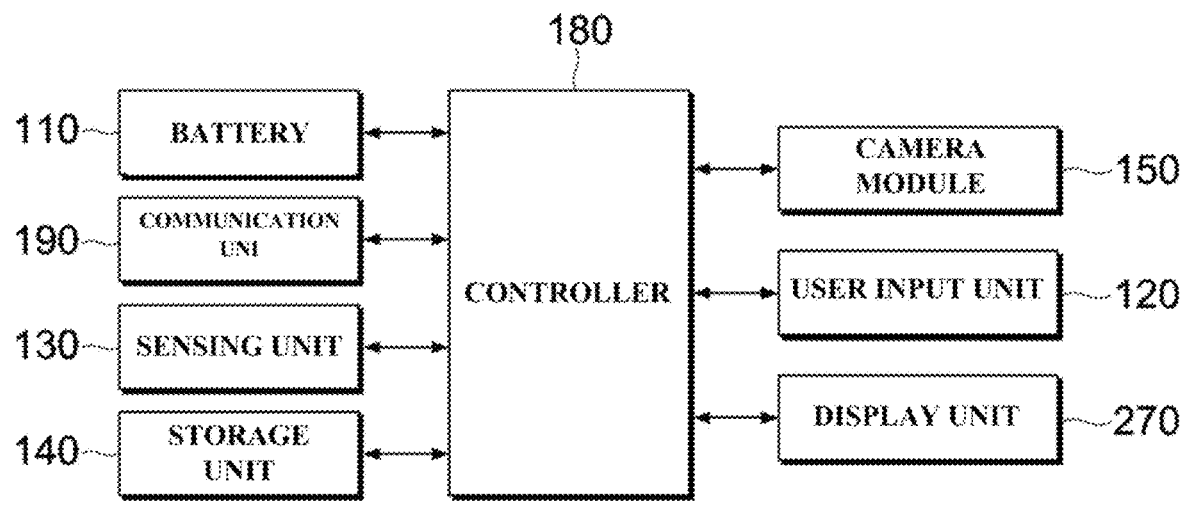

[FIG. 5]
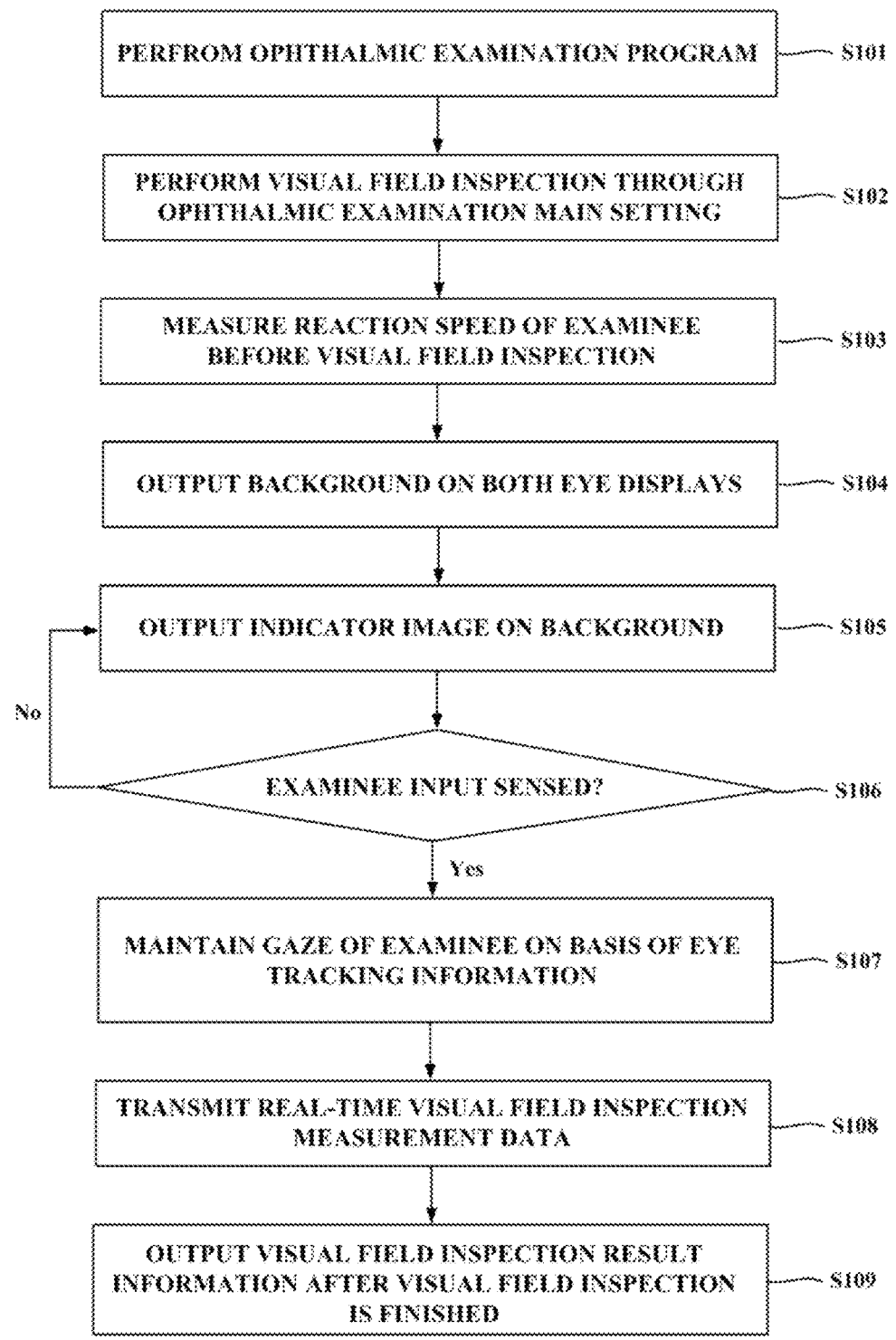

[FIG. 6]
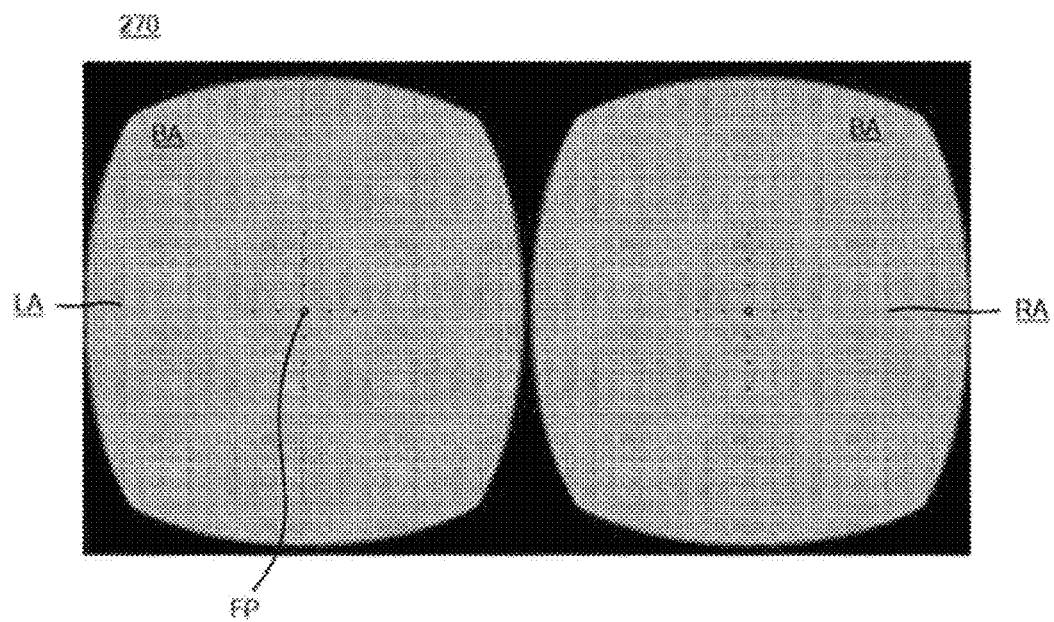
[FIG. 7]
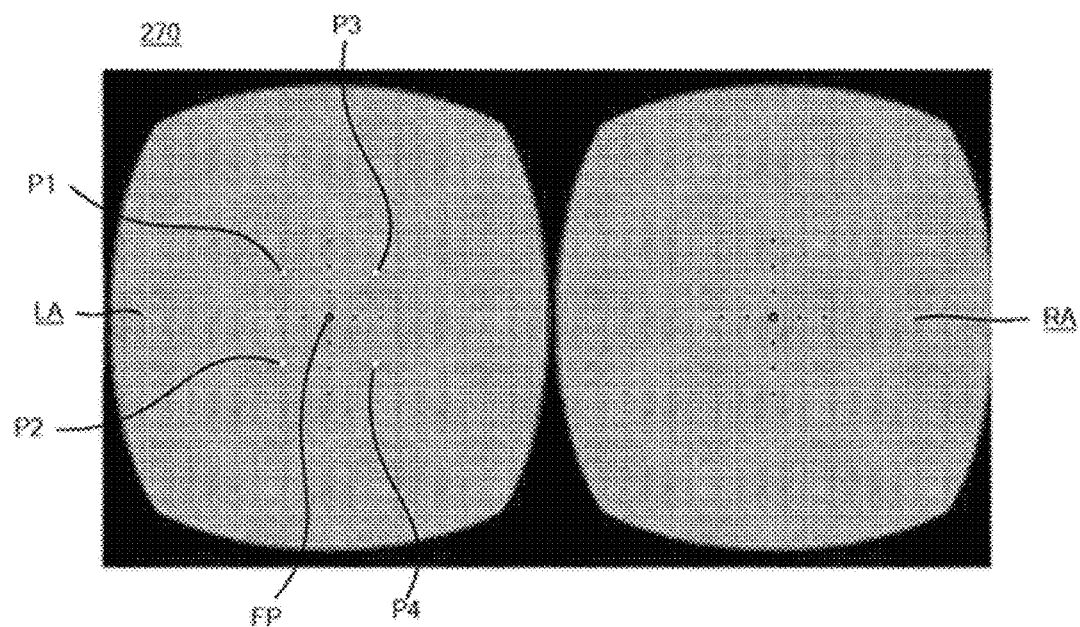

[FIG. 8]
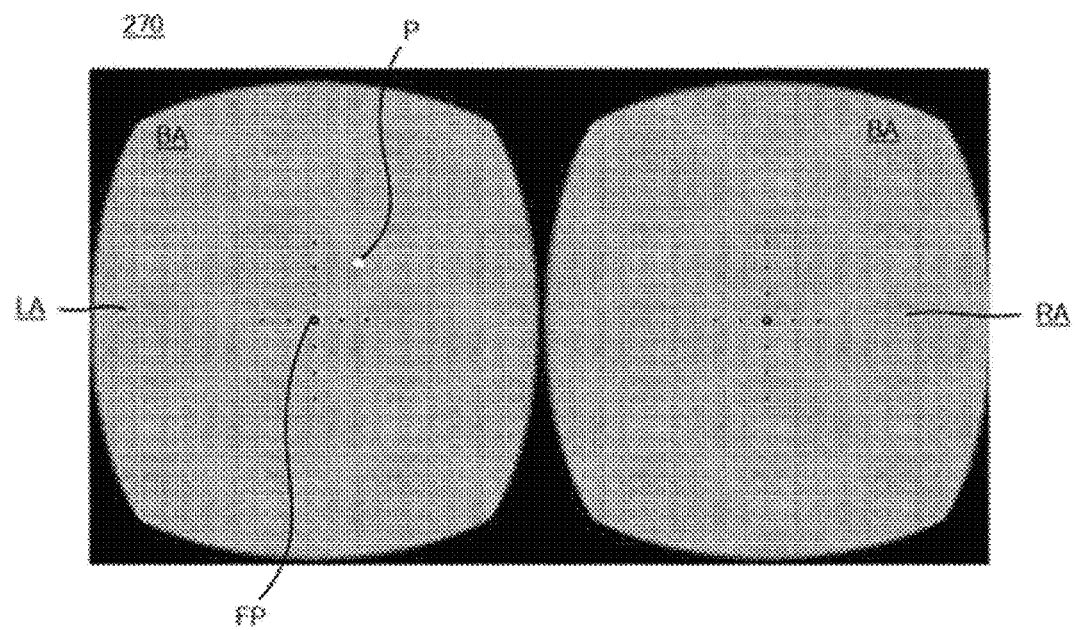

[FIG. 9]

[FIG. 10]
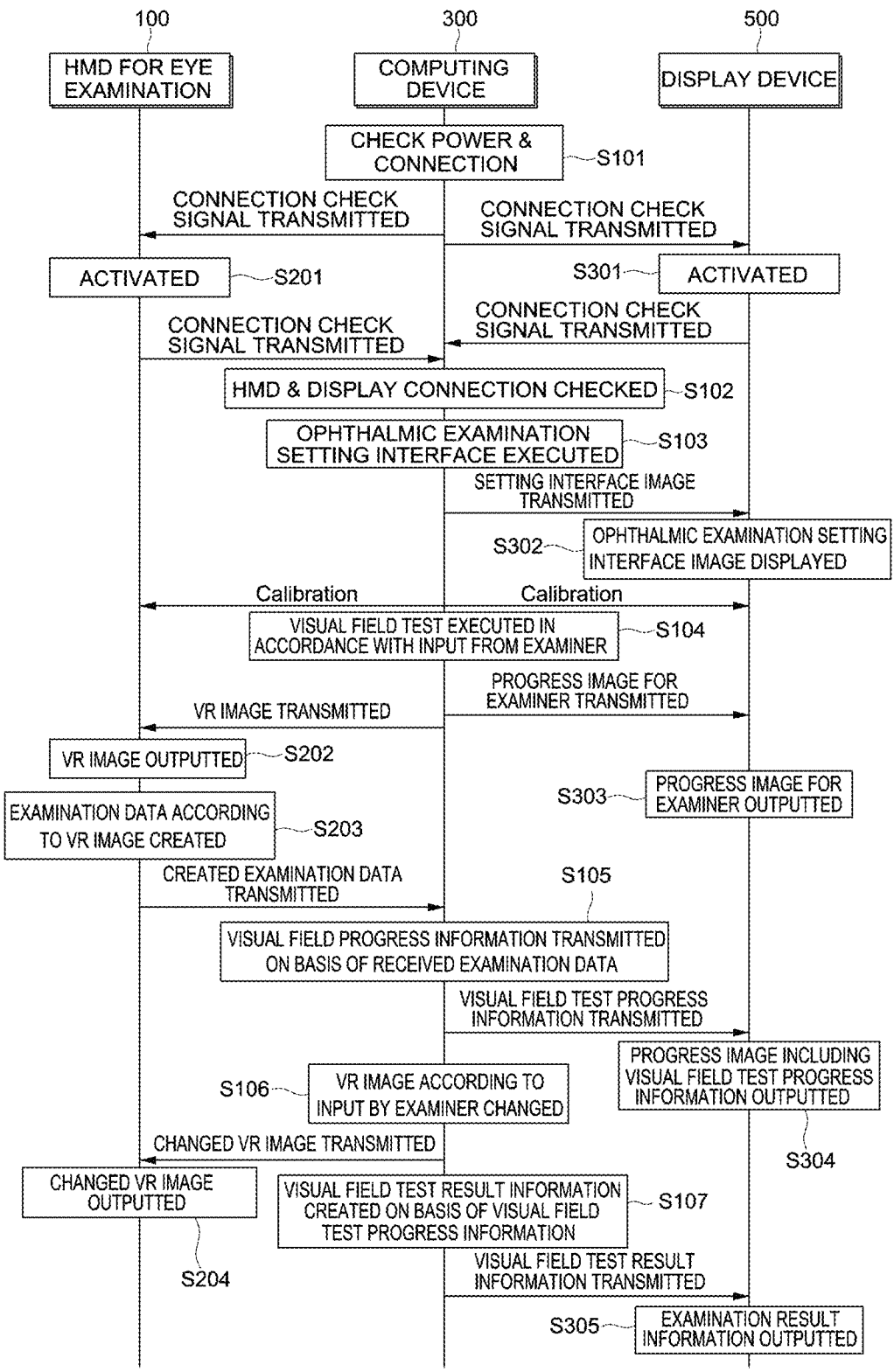

[FIG. 11]
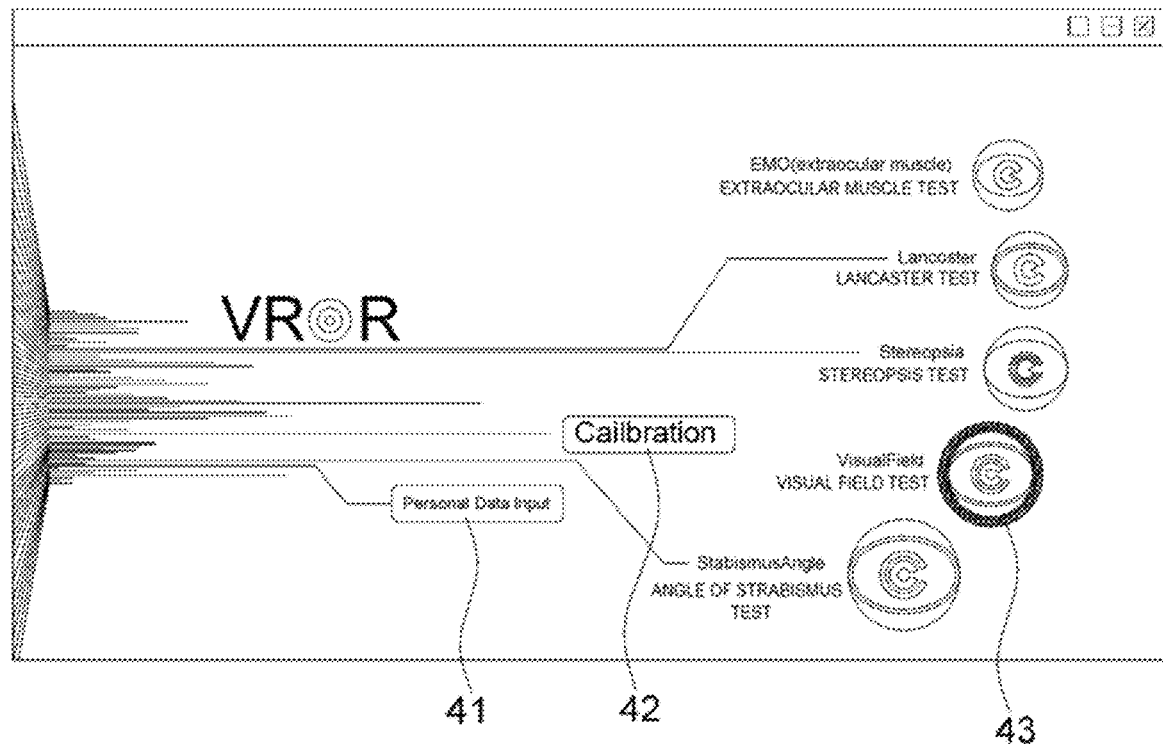
[FIG. 12]
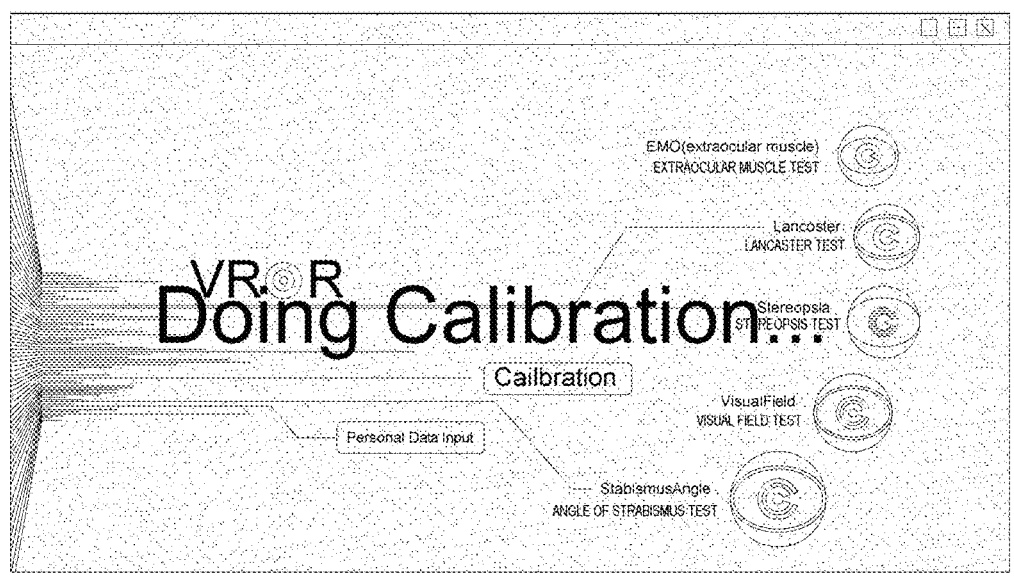

[FIG. 13]
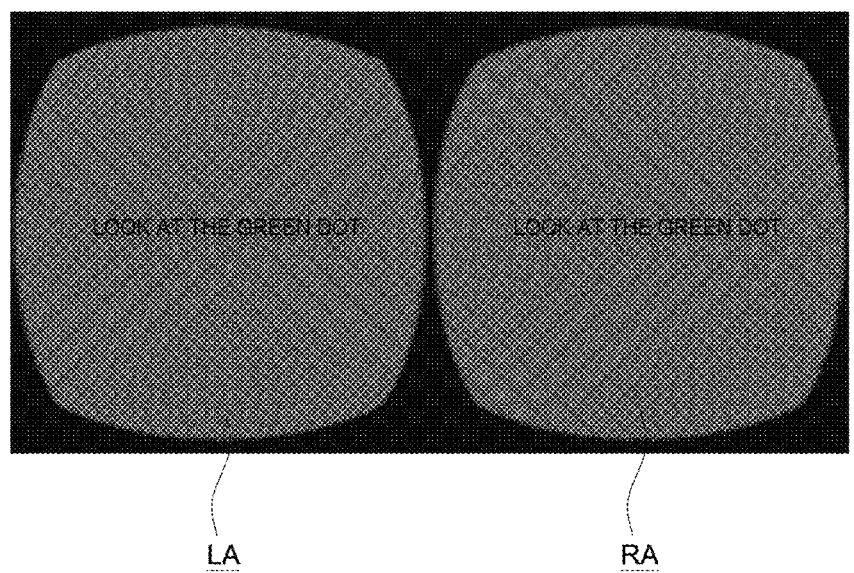
270
LA    RA

[FIG. 14]
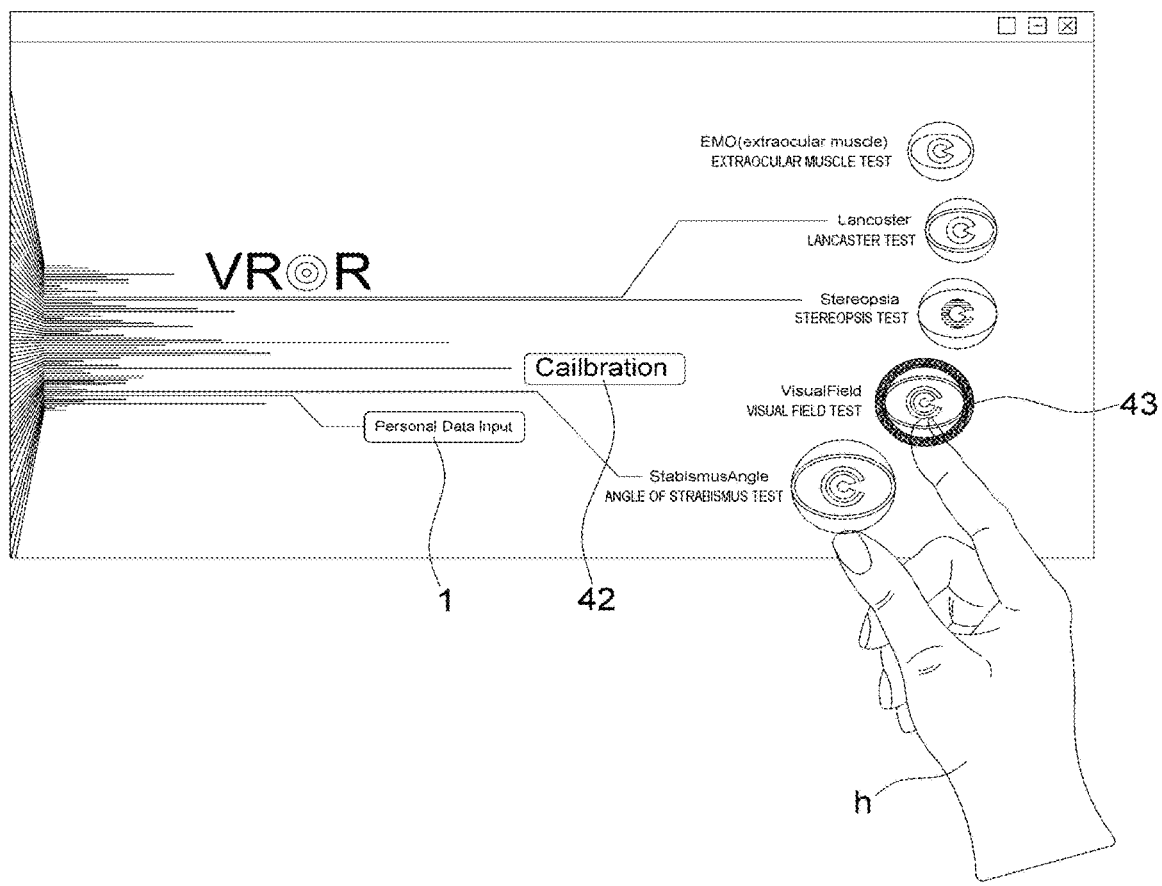

[FIG. 15]
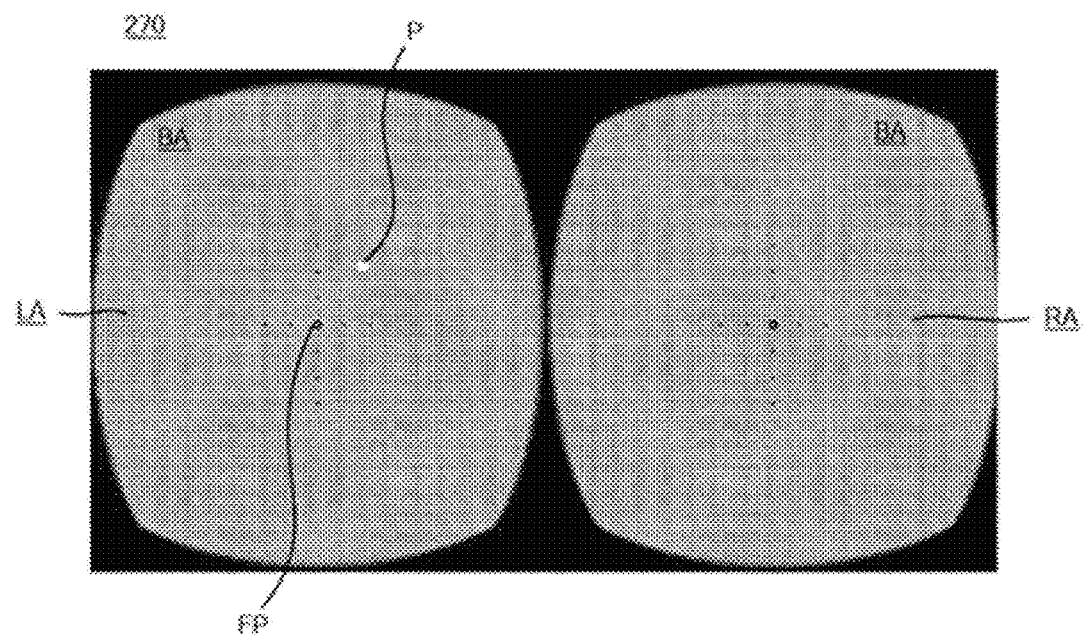

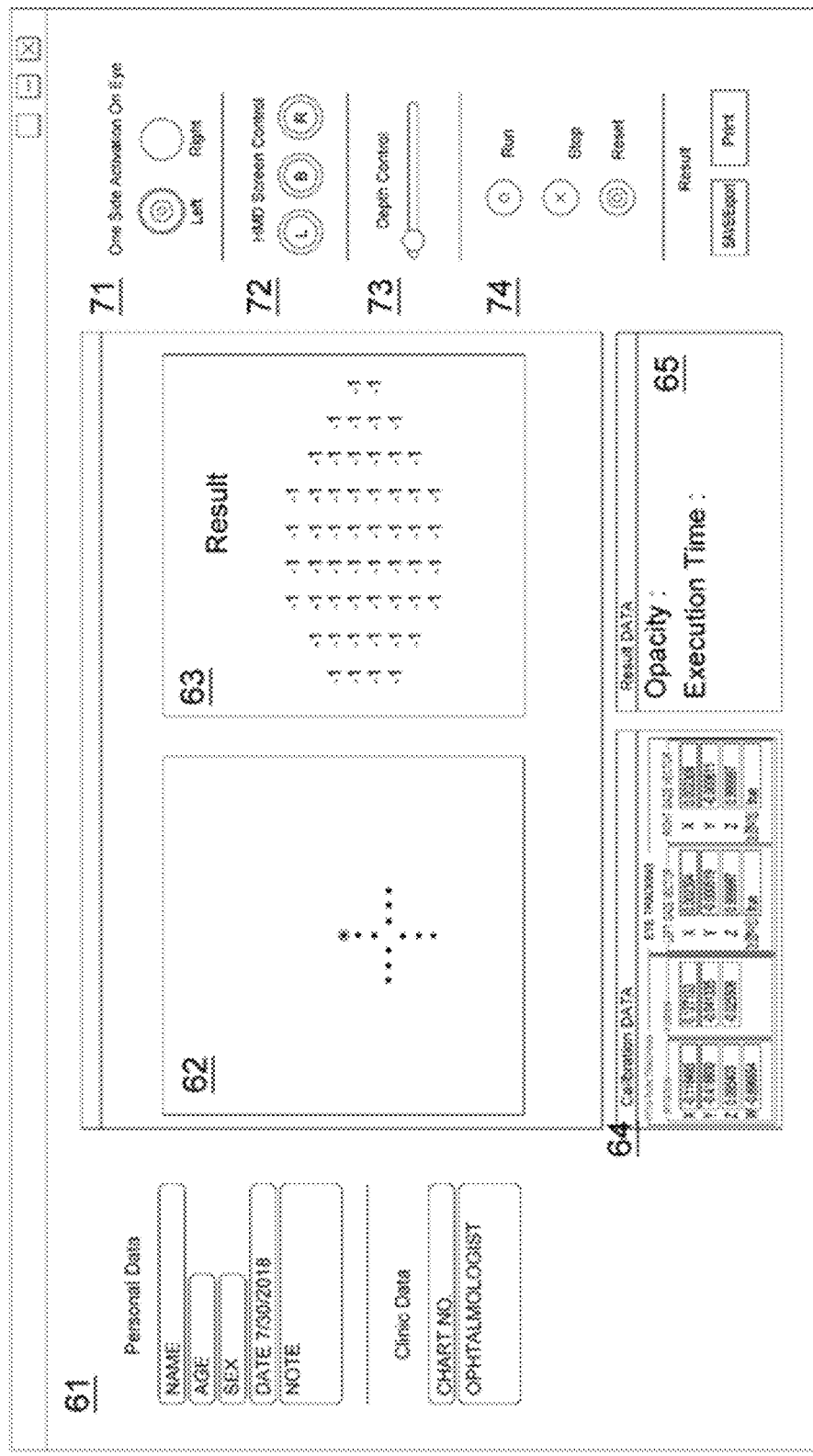
[FIG. 16]

[FIG. 17]
Visualfield VISUAL FIELD TEST RESULT PAPER
81 환자정보 Personal Data    의료정보 Clinic Data
NAME    Chart NO. 0001
AGE   SEX
DATA 7/6/2018
검사결과 Composition Analysis
82
Profile
Total Deviation
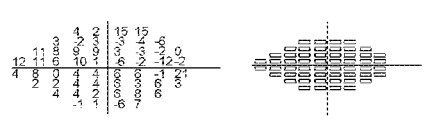
Pattern Deviation
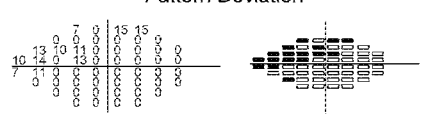
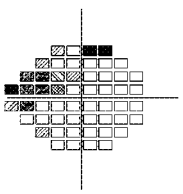
정상범위 Normal Range    의사소견 Medical Opinion
83 PART WITH WEAK OPTICAL NERVES IS SHOWN TO BE DARK
84 WRITE OPINION

METHOD AND SYSTEM FOR VIRTUAL REALITY-BASED VISUAL FIELD INSPECTION

CROSS-REFERENCE TO RELATED APPLICATIONS

This application is the U.S. National Phase under 35 U.S.C. § 371 of International Application No. PCT/KR2019/009158 filed on Jul. 24, 2019, which in turn claims the benefit of Korean Application Nos. 10-2018-0105160 filed on Sep. 4, 2018, 10-2018-0105193 filed on Sep. 4, 2018, and 10-2019-0005151 filed on Jan. 15, 2019, the disclosures of which are incorporated by reference into the present application.

BACKGROUND OF THE DISCLOSURE

Field of the Disclosure

The present disclosure relates to a method and system for virtual reality-based visual field inspection. In more detail, the present disclosure relates to a method and system for performing a visual field inspection by sensing a change of the eyeballs of an examinee that accompanies a virtual reality image.

Related Art

Many modern people have abnormal eyesight symptoms such as nearsightedness, farsightedness, and astigmatism, depending on personal, environment, and habitual factors. The ophthalmic disease of human is a concept including all problems such as a papillary problem and an eyeball movement problem in addition to abnormal eyesight.

In general, when an ophthalmic disease is suspected, a doctor or an optician performs an ophthalmic examination, and then when an ophthalmic disease is determined, a corresponding treatment is performed. For example, when there is a problem with eyesight, a doctor or an optician performs an eye test by applying light to a crystalline lens and checking the refractive index from the reflected light, and then corrects the eyesight using eyeglasses.

Since people show various ophthalmic disease symptoms, there are various examinations in the ophthalmic examination such as a visual field test, a stabismusangle test, an extraocular muscle test, a stereopsia test, or a Lancaster test.

A visual field is the visually shown limit of an external field that human can simultaneously see with both eyes on a specific target. A visual field inspection test is to measure the range of an external field that an examinee can see without moving the eyes when looking at any one point (hereafter, a focus point). That is, the visual field inspection is to measure the range of the central visual field, the range of the peripheral range, and the sensitivity threshold with the gaze of human fixed.

The object of measuring a visual field is to find out how much the limit of the range of eyesight generally or partially changes in comparison to the normal. The visual field inspection is an important test for diagnosing and observing the progress of not only central nervous system diseases, but, in terms of ophthalmology, glaucoma and diseases with the retina and the optic nerve.

However, methods of examining ophthalmic diseases in the related art are commonly manually performed by examining the eye state of an examinee (eye-disease patient) using expensive eye examination equipment by examiner (doctor or optician). Accordingly, there is a problem that, depending on the examiners, the test result of an examinee is not objective, a test takes long time, and a high test cost is required due to the personnel expenses of the examiners.

Further, although eye examination equipment for eye test of ophthalmic diseases has been substantially improved from the method that uses an eye chart in the related art, an examiner analyzes again the examination information of an examinee acquired by eye examination equipment and then determines the kinds of the ophthalmic diseases. Accordingly, there is a problem that it is difficult to quickly determine an ophthalmic disease on the basis of examination information.

Further, when an ophthalmic disease of an examinee is examined through eye examination equipment, there is a problem that the examinee is supposed not to move from the fixed position on the eye examination equipment until the examination is finished. That is, since the examination position for an ophthalmic disease of an examinee depends on eye examination equipment, the examination environment for the examinee is poor, including the case that the examinee has to take an ophthalmic examination in a stiffened state.

In particular, the visual field inspection requires a process of measuring how an examinee can react to light while tuning on and off light with different brightness many times to several visual field points with the gaze of the examinee fixed to a focus point. Accordingly, there is a problem that the examinee loses the power of concentration and does not keep the gaze on the focus point during the visual field inspection, so the accuracy of the inspection lowers and the fatigue of the examinee increases.

SUMMARY

An object of the present disclosure is to provide a digital method and system for a visual field inspection using VR that can solve the problems with the existing eye examination equipment.

In detail, an object of the present disclosure is to provide a digital method and system for a visual field inspection which perform a visual field inspection on the basis of a bundle of processes to be able to improve the accuracy of a visual field inspection and remarkably reduce the time required for a visual field inspection.

Another object of the present disclosure is to provide in real time the information about the process of a visual field inspection of an examinee and an input/output interface for an examiner according to the progress of the visual field inspection to an examiner in order to solve the problem that an inspection may be inefficiently performed when a visual field inspection is performed through the existing eye examination equipment.

Another objective of the present disclosure is to provide a digital method and system for a visual field inspection using a head-mounted display device that can perform various ophthalmic diseases as a single device in order to solve the problem that expensive eye examination equipment is required to perform a visual field inspection.

Another object of the present disclosure is to process data using an ophthalmic examination service provider server in the process of a visual field inspection based on virtual reality in order to reduce the time required to process large data in the process of a visual field inspection based on virtual reality and in order to easily perform an updated visual field inspection using the newest technology.

However, the objects to be achieved by the present disclosure and embodiments of the present disclosure are not limited to the object described above and there my be other objects.

A method for virtual reality-based visual field inspection according to an embodiment is a method that performs a visual field inspection on a head-mounted display. The method includes: outputting a background including a background image and a focus point image; outputting an indicator on the background; and sensing user input from an examinee according to output of the indicator.

The outputting of a background including a background image and a focus point image may include simultaneously displaying the background in a left eye area of a display unit and the background in a right eye image of the display unit.

The method may further include measuring a reaction speed of the examinee, in which the measuring of a reaction speed of the examinee may include calculating the reaction speed by outputting an indicator for measuring the reaction speed with predetermined brightness at a predetermined position in the background, and then sensing user input.

The method may further include calculating a visual field inspection result on the basis of the reaction speed, an output position of the indicator, a point in time of outputting the indicator, and a point in time of the user input.

The outputting of an indicator in the background may further include determining a position where the indicator is output in the background, and outputting the indicator at the position while controlling brightness of the indicator.

The outputting of the indicator at the position while controlling brightness of the indicator may include continuously and uniformly increasing the brightness of the indicator from the point in time of outputting the indicator.

The outputting of the indicator at the position while controlling brightness of the indicator may include controlling the brightness of the indicator by controlling transparency of a pixel showing the indicator.

The outputting of an indicator in the background may further include stooping output of the indicator and determining a position where a next indicator is output in the background when the user input is sensed while the brightness of the indicator is increased.

A method for virtual reality-based visual field inspection according to another embodiment, which performs a visual field inspection in an ophthalmic examination console device, includes: providing an ophthalmic examination setting interface for inputting user setting for an ophthalmic examination; performing a visual field inspection when the visual field inspection is selected from the interface; controlling a head-mounted display to output a virtual reality image for the visual field inspection; acquiring measurement data according to the virtual reality image from the head-mounted display; and outputting a visual field inspection progress image for an examiner for the visual field inspection.

The outputting of a visual field inspection progress image for an examiner may include outputting progress information of a visual field inspection that is progressed in real time, and the visual field inspection progress information may include at least one or more of personal information of the examinee, a visual field inspection VR image, the inspection data, analysis values according to the inspection data, and a real-time visual field inspection result value.

The visual field inspection VR image may include a graphic image obtained by converting a VR image output from the head-mounted display into 2D.

The outputting of a visual field inspection progress image for an examiner may further include providing an interface for controlling a visual field inspection on the basis of the analysis values according to the inspection data to an examiner.

The method may further include: acquiring visual field inspection result information on the basis of the measurement data matched to a VR image for the visual field inspection; and outputting the acquired visual field inspection result information.

The acquiring of visual field inspection result information on the basis of the inspection data may include: transmitting the measurement data to a visual field inspection service provider server; and receiving visual field inspection result information based on the measurement data from the visual field inspection service provider server.

Advantageous Effects

The method and system for virtual reality-based visual field inspection according to an embodiment of the present disclosure provides a method and system for a digital visual field inspection using a head-mounted display, so it is possible to quickly and accurately acquire a visual field inspection result of an examinee at a low cost.

Further, the method and system for virtual reality-based visual field inspection according to an embodiment of the present disclosure provides a method and system for a digital visual field inspection that performs a visual field inspection on the basis of a bundle of processes, so it is possible to remarkably reduce the time required for a visual field inspection.

Further, the method and system for virtual reality-based visual field inspection according to an embodiment of the present disclosure can perform a visual field inspection of an examinee in a normalized automatic inspection type, can acquire objective a visual field inspection data, and accordingly, can determine accurate ophthalmic diseases.

Further, the method and system for a virtual reality-based visual field inspection according to an embodiment of the present disclosure can enable an examiner to quickly and accurately perform a visual field inspection by providing in real time the information related to the visual field inspection process of an examinee and an input/output interface for an examiner according to the visual field inspection progress to the examiner.

Further, the method and system for virtual reality-based visual field inspection according to an embodiment of the present disclosure provides a method and system for a digital visual field inspection using a head-mounted display that is inexpensive in comparison to the existing eye examination equipment, so it is possible to perform a visual field inspection with high accuracy at a low cost.

Further, the method and system for virtual reality-based visual field inspection according to an embodiment of the present disclosure can perform a visual field inspection with an examinee wearing a head-mounted display in a comfortable posture, so it is possible to perform a visual field inspection of an examinee in a more comfortable environment.

Further, the method and system for virtual reality-based visual field inspection according to an embodiment of the present disclosure performs a visual field inspection through an ophthalmic examination service provider server, so it is possible to quickly progress an inspection by improving the data processing speed, it is possible to update and provide a newest visual inspection method, and it is possible to make a profit according to providing a service.

BRIEF DESCRIPTION OF THE DRAWINGS

FIG. 1 shows a system for virtual reality-based visual field inspection according to an embodiment of the present disclosure.

FIG. 2 is an internal block diagram of an ophthalmic examination console device of the system for virtual reality-based visual field inspection according to an embodiment of the present disclosure.

FIG. 3 is an exploded perspective view of a head-mounted display for an eye examination of the system for virtual reality-based visual field inspection according to an embodiment of the present disclosure.

FIG. 4 is an internal block diagram of the head-mounted display according to an embodiment of the present disclosure.

FIG. 5 is a flowchart illustrating a visual field inspection process based on virtual reality according to an embodiment of the present disclosure.

FIG. 6 shows a basic image that is output on a head-mounted display when a visual field inspection is performed on the basis of virtual reality in accordance with an embodiment of the present disclosure.

FIG. 7 shows indicator images that are output to measure a reaction speed of an examinee on the head-mounted display according to an embodiment of the present disclosure.

FIG. 8 shows an image output on the head-mounted display when a visual field inspection according to an embodiment of the present disclosure is performed.

FIG. 9 shows result information according to a visual field inspection according to an embodiment of the present disclosure.

FIG. 10 is a flowchart illustrating a visual field inspection process based on virtual reality according to an embodiment of the present disclosure.

FIG. 11 shows an ophthalmic examination main display image according to an embodiment of the present disclosure.

FIG. 12 shows an image that is output on a display device in calibration with the head-mounted display according to an embodiment of the present disclosure.

FIG. 13 shows an image that is output on a display device in calibration with the ophthalmic examination console device according to and embodiment of the present disclosure.

FIG. 14 shows an interface for selecting a visual field inspection according to an embodiment of the present disclosure.

FIG. 15 shows an image output on the head-mounted display while a visual field inspection according to an embodiment of the present disclosure is performed.

FIG. 16 shows an image output on a display device while a visual field inspection according to an embodiment of the present disclosure is performed.

FIG. 17 shows a test result image output on a display device after a visual field inspection according to an embodiment of the present disclosure is finished.

DESCRIPTION OF EXEMPLARY EMBODIMENTS

The present disclosure may be modified in various ways and implemented by various exemplary embodiments, so that specific exemplary embodiments are shown in the drawings and will be described in detail herein. The advantages and features of the present disclosure, and methods of achieving them will be clear by referring to the exemplary embodiments that will be describe hereafter in detail with reference to the drawings. However, the present disclosure is not limited to the disclosed embodiments and may be implemented in various ways. In the following embodiments, terms such as "first" and "second" are used to discriminate a component from another component without limiting the components. Further, singular forms are intended to include plural forms unless the context clearly indicates otherwise. Further, terms such as "include" or "have" mean that the features or components described herein exist without excluding the possibility that one or more other features or components are added. Further, components may be exaggerated or reduced in size for the convenience of description. For example, the sizes and thicknesses of the components shown the figures are selectively provided and the present disclosure is not necessarily limited thereto.

Hereinafter, embodiments of the present disclosure are described in detail with reference to the accompanying drawings, and in the following description of the accompanying drawings, like reference numerals are given to like components and repetitive description is omitted.

FIG. 1 shows a system for virtual reality-based visual field inspection according to an embodiment of the present disclosure and FIG. 2 is a block diagram of the system for virtual reality-based visual field inspection according to an embodiment of the present disclosure.

Referring to FIG. 1, an ophthalmic examination system using virtual reality according to an embodiment of the present disclosure may include an ophthalmic examination console device 300, 400, 500, a head-mounted display (HMD) 100, and an ophthalmic examination service provider server 700.

The components shown in FIGS. 1 and 2 may be connected through a network. The network means a connection structure enabling information exchange among nodes such as the ophthalmic examination console device, the head-mounted display 100, and the ophthalmic examination service provider server 700. For example, the network may include a 3GPP (3rd Generation Partnership Project) network, an LTE (Long Term Evolution) network, a WIMAX (World Interoperability for Microwave Access) network, the internet, a LAN (Local Area Network), a Wireless LAN (Wireless Local Area Network), a WAN (Wide Area Network), a PAN (Personal Area Network), a Bluetooth network, a satellite broadcasting network, an analogue broadcasting network, a DMB (Digital Multimedia Broadcasting) network, etc., but is not limited thereto.

Ophthalmic Examination Provider Server

First, the ophthalmic examination service provider server 700 can provide an interface for an ophthalmic examination process to an examiner through an ophthalmic examination console device by transmitting/receiving data for ophthalmic examinations to/from the ophthalmic examination console device through a network.

Further, the ophthalmic examination service provider server 700 can perform an ophthalmic examination on an examinee through the head-mounted display 100 through the ophthalmic examination console device or by directly transmitting/receiving data for ophthalmic examination to/from the head-mounted display 100 through a network.

In detail, the ophthalmic examination service provider server 700 can provide an examinee program for providing an interface for an examiner to perform an ophthalmic examination to the ophthalmic examination console device, and can improve the existing ophthalmic examination method by continuously updating an examiner program or can provide a new ophthalmic examination process, etc.

Similarly, the ophthalmic examination service provider server 700 can provide an examinee application for an ophthalmic examination to the head-mounted display 100, and can improve the existing examination method by continuously updating an examiner program or can provide a new ophthalmic examination process, etc.

Further, the ophthalmic examination service provider server 700 can provide data for performing an ophthalmic examination through the examinee program and the examiner application and can receive inspection data obtained by sensing reaction of an examinee to an ophthalmic examination, etc.

Further, the ophthalmic examination service provider server 700 can change the progress of an examination or can provide an examination result such that a user checks it, by analyzing the received inspection data and transmitting the analysis result to the ophthalmic examination console device and/or the head-mounted display 100.

That is, the ophthalmic examination service provider server 700 can improve the examination speed by minimizing data processing load that may be generated in the ophthalmic examination console device and/or the head-mounted display 100 by directly performing large-size deep learning, big data processing, etc. for ophthalmic examination analysis and then providing them to the ophthalmic examination console device and the head-mounted display 100, and can make inspection data continuously accumulated into big data and use the big data to improve the accuracy of examinations, the method of examinations, etc.

Further, the ophthalmic examination service provider server 700 can count and store the number of performing ophthalmic examination for each kind of ophthalmic examination, the number of analyzing inspection data, or the number of transmitting result data in a database, and can ask a user to pay for the services in accordance with the counted numbers stored in the database.

As a result, the ophthalmic examination service provider server 700 can minimize the data weight and the data processing load of programs/applications and can enable examinations to be quickly progressed by providing in real time data for ophthalmic examinations, an analysis result, etc. through a network, and can impose costs according to providing ophthalmic examination services in accordance with the examination kinds, the number of analysis processing, etc.

Hereafter, a process in which an ophthalmic examination is performed while the ophthalmic examination service provider server 700 communicates with the computing device of an ophthalmic examination console is described mainly about the computing device, but some of data analysis processed in the computing device is performed in the ophthalmic examination service provider server 700.

Head-Mounted Display

Next, the head-mounted display 100 according to an embodiment is a device that is worn on an examinee like wearing a helmet or eyeglasses and then can quickly and accurately examine ophthalmic diseases of the examinee using an optical unit and a display unit disposed in the head-mounted display 100.

In detail, the head-mounted display 100 according to an embodiment can output virtual reality (VR) images related to an ophthalmic examination from the ophthalmic examination service provider server 700 or/and the ophthalmic examination console device and can create reaction of examinee's eyes to the output VR images or/and input from the examinee as inspection data.

The VR image includes both of a 3D image and a 2D image and may be understood as including all images that can be output through the head-mounted display.

The head-mounted display 100 transmits the created inspection data directly or to the ophthalmic examination console device or/and the ophthalmic examination service provider server 700 and the transmitted inspection data may be used to derive an ophthalmic examination result. That is, the ophthalmic examination result may be acquired as inspection data.

According to the head-mounted display 100, an examinee can take an examination while freely moving or at a comfortable position without taking the examination in a state fixed to examination equipment of an examiner in a manual examination.

Further, the head-mounted display 100 of the present disclosure implements examination of ophthalmic diseases of an examinee in a wearable device type, whereby it is possible to examine ophthalmic diseases without specific ophthalmic examination equipment. Further, the head-mounted display 100 of the present disclosure can derive objective inspection data and can determine accurate ophthalmic diseases on the basis of the data by examining an ophthalmic disease of an examinee in a normalized automatic examination type.

For example, the head-mounted display 100 may be implemented as a wearable computer or may have the type of a wearable computer (or referred to as a wearable computing device). In an exemplary embodiment, the wearable computer may be a head-mountable display (HMD) or may include an HMD. The head-mounted display 100 may be any device that can be worn on the head and can show a display in front of one or both eyes of a wearer. The HMD may have various types such as a helmet or eyeglasses.

Referring to FIGS. 3 and 4, the head-mounted display 100 of the present disclosure may include the main body 200, and a display unit 270, an eye examination unit 250, an optical unit 220, an optical holder 210, a housing 160, an anti-optical interference unit 300, and a fixing band 170 that are sequentially disposed in the main body 200.

However, the components shown in FIGS. 3 and 4 are not necessary components of the head-mounted display 100, so they may not be provided, depending on embodiments. The rear surface of the main body 200 means the direction in which an opening is formed and the face of an examinee touches and the front surface of the main body 200 means the gaze direction of an examinee.

First, the main body 200 may be formed in a plastic and/or metallic solid structure or may be formed in a hollow structure made of similar materials such that wires and components are connected to each other to be internally routed through the head-mounted display 100.

Reference numeral '120' shown in the figures indicates a user input unit 120. The user input unit 120 can turn on/off the head-mounted display 100 or can sense input related to an ophthalmic examination.

In detail, the user input unit 120 can sense user input for performing communication between the head-mounted display 100 and an external system or can sense input for changing and selecting examination kinds when a user (examinee or examiner) performs an ophthalmic examination. Further, depending on cases, an alarm type LED light may be further included to make it possible to recognize the progress state of an examination or the state after an examination is finished from the outside.

Further, the head-mounted display 100 may further include an input unit wirely/wirelessly connected with the head-mounted display 100 and the input unit may be a device that senses input for deriving the intention of an examiner when an ophthalmic examination is performed. The input unit records the point in time of input and an input value by an examiner and transmits the recorded input value to the head-mounted display 100 or the ophthalmic examination console device and the transmitted input value may be included in the inspection data.

For example, the input unit may be a clicker and the clicker can transmit user input information to the head-mounted display 100 through communication when sensing pressing input by a user.

Next, a fixing band 170 is shown as two pieces of fixing band parts, but is not limited thereto. A helmet type may be provided to be able to fix the main body 200 to the face of an examinee or three or more bands may be provided to be able to fix the main body 200 while surrounding the head of an examinee.

Next, the display unit 270 may include at least one of a liquid crystal display (LCD), a thin film transistor liquid crystal display (TFT LCD), an organic light emitting diode (OLED), a flexible display, and an e-ink display.

The display unit 270 can finally display graphic images as 2D or/and 3D display to perform ophthalmic examinations.

For example, the display unit 270 can display VR images of 3D display and uses them for ophthalmic examinations. In detail, the display unit 270 can output a graphic image while changing the distance that a user feels for each output graphic image.

Further, when the panel of the display unit 270 is provided as a single display panel, separate images corresponding to the left eye and the right eye of an examinee respectively may be implemented. Depending on embodiments, the panel may be display panel separated into a left eye area and a right eye area.

Next, the eye examination unit 250 may include a plurality of sensors, a plurality of cameras, and a controller of the head-mounted display 100 and a circuit module that can communicate with external systems to be able to examine various ophthalmic diseases of examinees.

The eye examination unit 250 can perform an eye tracking function that tracks the eyes of an examinee who takes an eye test. To this end, cameras that can track movement of pupils of an examinee may be mounted in the eye examination unit 250.

The eye examination unit 250 can acquire inspection data that are the base for examining ophthalmic diseases such as a visual field test, a stabismusangle test, a extraocular muscle test, a stereopsia test, or a Lancaster test by tracking the gaze of an examinee that depends on VR images. In detail, the pupil image taken by the eye examination unit 260 may be included in the inspection data and transmitted to the ophthalmic examination console device or/and the ophthalmic examination service provider server 700 and the transmitted inspection data may be the base of the examination result.

That is, a light radiation unit, a photographing unit, etc. that are required for examinations such as a visual field test, a stabismusangle test, a extraocular muscle test, a stereopsia test, or a Lancaster test for examining ophthalmic diseases may be implemented in the type of a sensor module or a camera module.

Further, the eye examination unit 250 may include a sensor that can acquire refractive index information about the eyes of an examinee by radiating light to the left eye and the right eye of the examinee and receiving light for an eye test.

Next, the optical unit 220 is positioned between the eye examination unit 250 and the housing 160 and may provide the most suitable optical unit 220 corresponding to the kind of an ophthalmic examination of an examinee.

For example, when the ophthalmic examination of an examinee is an eye test, it is possible to selectively replace and fasten an optical lens for measuring the refractive index of crystalline lenses.

Further, when the ophthalmic examination of an examinee is a test that examines movement of pupils such as an extraocular muscle test, the optical unit 220 may be an optical lens that makes it possible to precisely see movement of pupils through a camera.

The optical unit 220 may be an optical unit having a structure in which several lenses having a polarization characteristic are stacked.

The optical unit 205 is fixed to the optical holder 210. Necessary optical units 250 may be replaced and detachably attached to the optical holder 210, depending on the kinds of ophthalmic examinations.

Next, the housing 160 is inserted in the direction of the opening of the main body 200 and fixes the display unit 270, the eye examination unit 250, the optical unit 220, the optical holder 210, or/and the main body 200 while maintaining optical alignment.

Further, it provides a space between the display and both eyes of an examinee in which an ophthalmic examination can be performed when the examinee wears the head-mounted display 100.

Accordingly, the inside of the housing 160 may include a left eye area and a right eye area that is independently separated by the anti-optical interference unit 300.

Further, the inner surface of the housing 160 may be coated with a material having low light reflection and a high light absorption ratio for ophthalmic examinations.

Next, the anti-optical interference unit 300 can separate the head-mounted display 100 into a left eye area and a right eye area for ophthalmic examinations of an examinee. In general, people have two eyes with similar shapes at similar positions, but each eye independently functions, so ophthalmic diseases also show similar but slightly different symptoms. Accordingly, there are tests for independently performing ophthalmic examinations for the left eye and the right eye.

However, when light that is used during an ophthalmic examination for the left eye influences the adjacent right eye or vice versa, it is difficult to accurately and precisely examine an ophthalmic disease. For example, when only the left eye is examined with the right eye covered or vice versa, if the light output from an area interferes with the other area, it may have a bad influence on the examination result.

Accordingly, the head-mounted display 100 according to an embodiment includes the anti-optical interference unit 300, thereby being able to block light generated in the left eye area and the right eye area from invading areas each other.

That is, the head-mounted display 100 in an embodiment physically separates the left eye area and the right eye area of the display unit 270 when being worn on the head of a user through the anti-optical interference unit 300 and the housing 160, thereby being able to prevent the light output from the left-area display from entering to the light eye area and prevent the light output from the right-eye display from entering the left eye area.

Accordingly, when an ophthalmic examination is performed by the head-mounted display 100 according to an embodiment, the examination can be performed without the examinee closing the right eye even though the ophthalmic examination is performed on the left eye. In detail, when an ophthalmic examination is performed on the left eye, the head-mounted display 100 can perform the ophthalmic examination on the right eye too while maintaining the other environment in the same way (e.g., output the same background as that for the left eye) except for the image display for the examination.

When a person closes one eye, he/she may feel inconvenient for a long-time ophthalmic examination and the accuracy of the ophthalmic examination may be deteriorated by the influence on the other eye due to the closed eye.

Accordingly, the anti-optical interference unit 300 may include an optical block 301 that separates the head-mounted display 100 into the left eye area and the right eye area and blocks the light traveling to an adjacent area from each area.

In order to further increase the optical block ratio, the anti-optical interference unit 300 may include a contact-optical block 302 for preventing optical interference that is generated at the optical block 301 and the region (the brow) between the left eye and right eye areas of an examinee when the examinee wears the HMD for an eye examination, and may further include a first fixing portion 304 and a second fixing portion 305 that fix and support the anti-optical interference unit 300 in the brow region and the nose ridge region of the examinee.

Accordingly, the optical block 301 is not simply supported by the nose of a wearer and has a shape corresponding to the shape between the brow and the philtrum, so it is possible to prevent light leakage between the left eye area and the right eye area by separating the left eye area and the right eye area when the head-mounted display 100 is worn.

Further, it is preferable that the optical block 301 and the contact-optical block 302 are made of a material having small light reflection and a high light absorption ratio. Further, since the contact-optical block 302 is a part that is supposed to come in contact with the face skin of an examinee, it is preferable that the contact-optical block 302 is made of a material having a high shock absorption ability.

Since the left eye area and the right eye area are optically separated in the area for examining ophthalmic examinations in the head-mounted display 100 of the present disclosure, there is an effect that it is possible to prevent examination errors due to optical interference that may be generated during examinations.

Further, referring to FIG. 4, in terms of function, the head-mounted display 100 according to an embodiment may include a battery 110, a communication unit 190, a sensing unit 130, a storage unit 140, a camera module 150, a user input unit 120, a display unit 270, and a controller 180.

However, the components shown in FIG. 4 are also not necessary parts, so the heat-mounted display 100 may be composed of more or less components. Hereafter, the components are sequentially described.

First, the controller 180 usually controls the general operation of the head-mounted display 100. For example, it is possible to transmit/receive various signals or process input data by controlling the communication unit 190.

Further, it can provide information to an examinee or an examiner by controlling an image output unit and a sound output unit that may be disposed in the display unit 270.

Depending on embodiments, the head-mounted display 100 may extract inspection data obtained by examining the eyes of an examinee, may perform comparison and direct calculation on the basis of the ophthalmic disease data stored in the storage unit 140, and then may determine the ophthalmic disease of the examinee.

The battery 110 is controlled by the controller 180 to be provided with external power and internal power and to supply power for the operation of the components.

For example, the battery 110 may include a battery, a connection port, a power supply controller, and a charge monitoring unit.

The camera module 150 processes image frames such as still images or moving images taken by an image sensor in a video call mode or a photographing mode. The processed image frames can be stored in the storage unit 140 or transmitted to an external system through the communication unit 190.

At least two or more camera modules 150 may be provided, depending on the examination kind or examination environment of the ophthalmic disease of an examinee.

For example, when an examinee takes an eye test, a camera may be used to monitor the pupils. Further, when movement of the eyeballs of an examinee is tracked, a camera that can take photographs along the movement path of the eyeballs may be used.

The communication unit 190 enables wire/wireless communication with the ophthalmic examination console device or/and the ophthalmic examination service provider server 700 that is an external system. The external system may be a concept including another head-mounted display 100.

The communication unit 190 may include a mobile communication module, a wireless internet module, a short range communication module, and a position information module.

The sensing unit 130 may include a gyro sensor that senses the surrounding environment, an acceleration sensor, a proximity sensor, etc.

In particular, the head-mounted display 100 of the present disclosure may include at least two or more optical sensors that generate light to be radiated to the eyes of an examinee and receive light to examine an ophthalmic disease.

The storage unit 140 can keep applications for processing and controlling by the controller 180 and can also temporarily store input/output data.

Ophthalmic Examination Console Device

Referring to FIGS. 1 and 2, the ophthalmic examination console device according to an embodiment may include a console body 121, a display device 500, an input device 400, and a computing device 300.

First, the console body 21 may be an external body supporting the display device 500, the input device 400, and the computing device 300.

In detail, a carrying unit 31, 32 supporting the main body of the console body 21 and enabling an examiner to easily move the console body 21 may be disposed at the lower end of the console body 21.

For example, the carrying unit 31, 32 may include at least one wheel that comes in contact with the ground and may include at least one support connecting the wheel and the main body.

The main body may include a holder 22 that can hold the input device 400 and a bed supporting the display device 500. The holder 22 can be drawn in and out of the bed, so it may be configured to improve space usability.

A keyboard 401 and/or a mouse 402 may be disposed as the input device 400 on the holder 22, and the input device 400 is connected with the computing device 300 through a wire/wireless interface, thereby being able to sensing and transmitting input for examinations by an examiner to the computing device 300.

The console body 21 may further include a first height adjuster 12 for adjusting the height of the bed and a second height adjuster 11 for adjusting the height of the display device 500 disposed on the bed.

In detail, the first height adjuster 12 is coupled to the bed by sliding, whereby it is possible to increase or decrease the height of the position of the bed by applying a force to the bed for unlocking.

Similarly, the second height adjuster 11 is coupled to the display device 500 by sliding, whereby it is possible to increase or decrease the height of the position of the display device by applying a force to the display device 500 when unlocking.

The display device 500 is disposed on the bed and can output graphic images for performing an ophthalmic examination by an examiner.

In detail, the display device 500 can output graphic images, etc. related to an interface for an examiner to perform an ophthalmic examination, an ophthalmic examination result, and control of the head-mounted display.

That is, the display device 500 according to an embodiment can provide an ophthalmic examination graphic user interface for an examiner in cooperation with the input device 400.

The display device 500 can be controlled by the computing device 300 to output necessary graphic images, and to this end, the display device 500 can be connected to the computing device through a wire or wirelessly.

A touch input sensor is further disposed on the display panel of the display device 500 and an input/output interface sensing touch input by an examiner is provided, whereby an examination can be more quickly and intuitionally performed.

The display device 500 may include at least one of a liquid crystal display (LCD), a thin film transistor liquid crystal display (TFT LCD), an organic light emitting diode (OLED), a flexible display, and an e-ink display.

The computing device 300 may include a main processor 360 disposed in the main body 21 and performing ophthalmic examinations by controlling the display device 500, the input device 400, the head-mounted display 100, etc.

In detail, referring to FIG. 2, the computing device 300 according to an embodiment may include a communication unit 370, an input unit 310, an interface unit 320, a memory 330, an output unit 340, a power unit 350, and a processor 360.

First, the communication unit 370 can transmit/receive data for ophthalmic examinations through a network by communicating with an external system, particularly, the ophthalmic examination service provider server 700.

For example, the communication unit 370 can transmit/receive wireless signals through a network constructed on the basis of GSM (Global System for Mobile communication), CDMA (Code Division Multi Access), HSDPA (High Speed Downlink Packet Access), HSUPA (High Speed Uplink Packet Access), LTE (Long Term Evolution), LTE-A (Long Term Evolution-Advanced) etc.), WLAN (Wireless LAN), Wi-Fi (Wireless-Fidelity), and Wi-Fi (Wireless Fidelity), or can transmit/receive wireless signals through short range communication such as RFID and NFC.

Next, the input unit 310 may be an input unit 310 for turning on/off the power of the computing device 300, and for example, may be a button.

Further, the interface unit 320 may be a data passage for data communication with an external device such as the display device 500, the input device 400, or/and the heat-mounted display 100.

In detail, the interface unit 320 is connected with various ports and/or cables through wires, thereby being able to connecting external devices and the computing device 300.

The interface unit 320 is a short range wireless communication module such as Bluetooth or WiFi and can perform data communication with an external device through short range wireless communication.

Next, the memory 330 can store any one or more of application programs, data, and commands for ophthalmic examination functions according to an embodiment.

The memory 330 may be various storage devices such as a ROM, a RAM, an EPROM, a flash driver, a hard drive, and may be a web storage that performs the storage function of the memory 330 on the internet.

Finally, the processor 360 can control general operations of the units described above to provide various examiner interfaces for an examiner to perform ophthalmic examinations.

The processor 360 can be realized using at least one of application specific integrated circuits (ASICs), digital signal processors (DSPs), digital signal processing devices (DSPDs), programmable logic devices (PLDs), field programmable gate arrays (FPGAs), controllers, micro-controllers, microprocessors, and electronic units for executing other functions.

Method for Visual Field Inspection Based on Head-Mounted Display

Hereafter, a method of performing a visual field inspection through a heat-mounted display is described with reference to FIGS. 5 to 9. Hereafter, in an embodiment, a head-mounted display performs a visual field inspection by directly processing data. In another embodiment, the head-mounted display described above may perform a visual field inspection by controlling an ophthalmic examination service provider server or/and an ophthalmic examination console device.

First, the head-mounted display 100 can execute an ophthalmic examination program (S11).

In detail, with the head-mounted display 100 worn on an examinee, an examiner or the examinee can activate the display through the user input unit 120 or/and the ophthalmic examination console device and execute an ophthalmic examination program.

When the ophthalmic examination program is executed, the head-mounted display 100 displays an ophthalmic examination setting interface, and when a visual field inspection is selected by a user from the ophthalmic examination setting interface, a visual field inspection can be started (S12).

In detail, an examiner can select execution of a visual field inspection from the ophthalmic examination setting interface through the user input unit 120 of the head-mounted display 100 or the input device 400 of the ophthalmic examination console device.

Further, it is possible to input examinee information, perform calibration with the ophthalmic examination console device, and select one of a plurality of ophthalmic examinations through the ophthalmic examination setting interface.

Calibration setting may be work for focusing the examinee wearing the head-mounted display 100. In detail, the head-mounted display 100 displays pointers with the left eye and right eye areas separated and displays a message making an examinee look at the pointers to focus the examinee on the pointers, thereby being able to perform calibration setting.

Next, the head-mounted display 100 can measure the reaction speed of an examinee before performing a main visual field inspection process (S13).

In detail, an indicator is displayed on the display unit, user input of an examinee for the indicator is guided through the user input unit 120, and a visual field inspection may be performed on the basis of the user input for the indicator.

For example, an examinee recognizes an indicator with the gaze fixed to the focus pint and then presses the user input unit 120 (e.g., a clicker), whereby a visual field inspection can be performed.

Hereafter, the time until an examinee performs input through the user input unit 120 after reacting to an indicator is determined as a reaction speed.

However, since the reaction speeds of people are all different, it may be difficult to obtain an accurate examination result when performing a visual field inspection without considering the reaction speed of an examinee.

Accordingly, the head-mounted display 100 can improve the accuracy of a visual field inspection for each examinee by measuring the reaction speed of an examinee before the visual field inspection and then considering the reaction speed when calculating a visual field inspection result.

In detail, the head-mounted display 100 can output at least one or more times an indicator with predetermined brightness at a predetermined position in the same environment as that for a visual field inspection and can calculate a reaction speed on the basis of the difference of the points in time of input by the user when the indicator is output and after the indicator is output.

The predetermined position is a position where people can most conveniently recognize an indicator. Referring to FIG. 7, the position where an indicator for measuring a reaction speed may include at least one of positions P1, P2, P3, and P4 respectively spaced 9 degrees in left upper, left lower, right upper, and right lower direction from a focus point that is 0 degrees.

It may be preferable that the predetermined brightness is middle brightness of the entire brightness that can be output so that a user sufficiently recognize it and a visual field inspection is not influenced later.

The same environment, as shown in FIG. 6, means the state in which the background output on the both eye displays and a focus point image on the background are displayed in the same way when a visual field inspection is performed.

For example, the head-mounted display 100 may sense input by an examinee after turning on/off an indicator for measuring a reaction speed with middle brightness one time at 9 degrees in the left upper direction from the focus point on a background, and then may measure the difference the point in time of outputting the indicator for measuring a reaction speed and the point in time of input by the examinee.

In order to more accurately measure a reaction speed, the head-mounted display 100 outputs indicators for measuring a reaction speed sequentially at 9 degrees in the left upper, left lower, right upper, and right lower directions from the focus point and then sense user input for each of the indicators, thereby being able to measure the reaction speed of the examinee.

When obtaining the difference a plurality of points in time of outputting indicators and of inputting, the head-mounted display 100 may set the minimum time difference as a reaction speed.

In other embodiment, when obtaining the difference a plurality of points in time of outputting indicators and of inputting, the head-mounted display 100 may set the average time difference as a reaction speed of an examinee.

The reaction speed measured in this way may be transmitted to the ophthalmic examination or/and the ophthalmic examination service provider server 700.

Next, the heat-mounted display 100 may perform a visual field inspection by outputting a VR image related to the visual field inspection on both eye displays.

In detail, the heat-mounted display 100 can output a background on both eye displays (S14).

In detail, the heat-mounted display 100 can display a background showing a focus point (FP) image including a focus point (FP) and a sub-point making the focus point (FP) conspicuous on a background image (BA) having predetermined chroma and brightness.

The background image (BA) may have at least one of ivory, gray, and green colors that do not make eyes tired.

The focus point (FP), which is an image showing the point on which the examinee focuses his/her gaze, may be a point shown at the center of the head-up display. Sub-points for inducing the focus to the focus point (FP) may be further displayed around the focus point (FP).

That is, with an examinee keeping a gaze on the focus point, indicators are output at different positions on the background and a visual field may be performed to check whether examinee recognizes the indicators.

Using the advantage of the head-mounted display of an embodiment that can output different images for both eyes and in which both eye sides are independently separated such that light output from a side does not influence the other side, the head-mounted display 100 can output the same background to the left eye and the right eye so that the examinee recognizes that he/she see the same background through the left eye and the right eye.

For example, referring to FIG. 6, the display unit 270 of the head-mounted display 100 can output a background including a background image (BA) and a focus point (FP) on each of a left eye area display LA and a right eye area display RA.

AS described above, the head-mounted display 100 providing the same environment to both eye sides can perform a visual field inspection for the left eye with an examinee opening the right eye even in a visual field inspection of the left eye. On the contrary, the head-mounted display 100 can perform a visual field inspection with an examinee opening the left eye even in a visual field inspection of the right eye.

That is, a visual field inspection according to an embodiment can be performed while maintaining the same environment excepting indicator display for an examination for the other eye when a visual field inspection is performed for one eye. Accordingly, it is possible to improve the accuracy of a visual field inspection and minimize inconvenience due to the inspection for the examinee.

Next, with the background output, the head-mounted display 100 can output an indicator to the eyeball to be examined (S15).

In detail, the head-mounted display 100 can output an indicator at a random position on the background of one area.

In more detail, when the head-mounted display 100 displays points on a background, the points within a predetermined distance from the focus point (FP) may be positions where indicators are displayed. The head-mounted display 100 may randomly select one of positions where indicators are displayed, and then output a indicator at the selected position.

Accordingly, the smaller the sizes of the points, the higher the resolution, so the precision of a visual field inspection can be improved, but the inspection may take long time. On the contrary, when the sizes of points are increased, the resolution is decreased, so the precision of a visual field inspection is decreased, but the inspection time may be decreased.

The head-mounted display 100 has to gradually control the brightness of an indicator when outputting the indicator to perform a visual field inspection. The brightness of an indicator means the luminance of light output from a pixel showing the indicator.

In detail, the head-mounted display 100 can gradually increase the brightness of an indicator after outputting the indicator with relatively low brightness at the point in time of outputting the indicator.

For example, the head-mounted display 100 can output an indicator with the lowest brightness at the point in time of outputting the indicator and then can increase the brightness at a predetermined speed until user input is applied.

In another meaning, the head-mounted display 100 can display an indicator such that the brightness of the indicator is linearly increased.

The head-mounted display according to an embodiment can control the brightness of an indicator by changing the display vector showing the indicator in order to gradually increase the brightness of the indicator.

In detail, the display unit 270 of the head-mounted display 100 can control the brightness of an indicator by changing the in-pixel transparency a of the pixel showing the indicator.

For example, assuming that the transparency a of the factor showing an indicator is 0 to 255, the display unit 270 of the head-mounted display 100 can continuously and uniformly increase the brightness of the indicator by gradually increasing the transparency of the pixel from 0.

That is, the display unit 270 according to an embodiment can control the brightness of an indicator to be uniformly increased by continuously and uniformly increasing the transparency of the pixel showing the indicator.

In another embodiment, the display unit 270 may control the brightness of an indicator by increasing or decreasing in-pixel R, G, B values of the pixel showing the indicator.

Meanwhile, in another embodiment, the head-mounted display 100 can reduce the visual field inspection time by controlling the speed of increasing the brightness of an indicator. For example, in another embodiment, the head-mounted display 100 can further reduce the progress time of a visual field inspection by quickly increasing the brightness of an indicator in a low-brightness period of the indicator in which human does not recognize the indicator well and by slowly increasing the brightness of the indicator in a middle-brightness period in which human generally recognizes the indicator.

After an indicator is output, the head-mounted display 100 can sense input by a user (S16).

In detail, the head-mounted display 100 can sense user input (e.g., clicker input) while an indicator is output and the brightness is gradually increased. That is, an examinee will recognize an indicator when the brightness of the indicator reaches a level at which the examinee can recognize the indicator, and in this case, the examinee can check the point in time of recognizing the indicator as a point in time of user input by pressing the user input unit 120.

The head-mounted display 100 sensing the user input can store the point in time of outputting the indicator that is the point in time at which the indicator is initially output and the point in time of user input as visual field inspection measurement data, and can transmit the data to the ophthalmic examination console device or the ophthalmic examination service provider server 700.

When the user input is sensed, the head-mounted display 100 stops outputting the output indicator, and then randomly determines a position where an indicator has not been output and outputs the next indicator, thereby being able to progressing the visual field inspection.

That is, the head-mounted display 100 randomly selects a position where a visual field inspection is performed on a background, outputs an indicator while increasing the brightness, and senses user input for the indicator, thereby performing the visual field inspection. When indicators are output at least one time at all positions where a visual field inspection is performed, the visual field inspection may be finished.

While a visual field inspection is performed, the head-mounted display 100 can check whether the focus of the examinee is maintained at the focus point (FP) on the basis of eye tracking information (S17).

In detail, the head-mounted display 100 can measure the focus according to the positions of the pupils of a user when calibration examination, and accordingly, it is possible to continuously check whether the focus of an examinee is maintained at the focus point (FP). Accordingly, the head-mounted display 100 can accurately sense the moment when the focus of an examinee comes out of the focus point (FP), and can stop the visual field inspection and output an alarm using a graphic image or audio such that the examinee maintains the focus on the focus point (FP).

The head-mounted display 100 can improve the accuracy of the visual field inspection by nullifying the data measured when the focus of the examinee comes out of the focus point (FP).

When the visual field is progressed, the head-mounted display 100 can transmit the measurement data measured in real time in accordance with the visual field inspection to the ophthalmic examination console device or/and the ophthalmic examination service provider server 700 (S18).

In detail, the head-mounted display 100 can transmit the indicator output position, the point in time of outputting an indicator, and the point in time of user input in real time to the ophthalmic examination console device or/and the ophthalmic examination service provider server 700.

A real-time visual field inspection result value can be calculated on the basis of the measurement data measured in this way.

For example, the ophthalmic examination console device can calculate light sensitivity threshold in consideration of the reaction speed for the difference between point in time of outputting an indicator and the point in time of input for the indicator position.

The ophthalmic examination console device can show the light sensitivity threshold calculated in real time at the indicator position so that the examiner monitors in real time the progress situation of the visual field inspection for the examinee through the ophthalmic examination console device.

When indicators are output at all visual field inspection positions, the visual field inspection is finished and the head-mounted display 100 can output visual field inspection result information (S19).

In detail, as shown in FIG. 9, the visual field inspection result information may include personal information 81 of the examinee, a visual field inspection result value 32, and/or eyeball state information based on the field inspection result value 82, etc.

In detail, a graph showing the light sensitivity threshold at each visual field inspection position may be displayed as the field inspection result value.

As the eyeball state information based on the visual field inspection result value, values such as WIthin normal limit, Borderline, Outside normal limits and indexes such as VFI, MD, and PSD may be displayed.

The visual field inspection result information may be made in the ophthalmic examination console device or/and the ophthalmic examination service provider server 700. Depending on embodiments, it may be directly performed in the controller of the head-mounted display 100.

In the process of calculating visual field inspection result information, the information about values obtained by tracking the positions of the pupils from an eyeball image, the position information of the eyeballs, the information obtained through image-deep learning of eyeball reaction, sensed measurement data, analysis values according to inspection data, and/or real-time visual field inspection result values may be included, and the visual field inspection result information is calculated in accordance with these items of objective information, so the visual field inspection result information can be accurate and precise.

The method for a virtual reality-based visual field inspection according to an embodiment provides a digital visual field inspection based on a bundle of processes, so it is possible to perform a visual field inspection of an examinee in a normalized automatic inspection type, obtain objective visual field inspection data, and accordingly, it is possible to accurately determine ophthalmic diseases.

In particular, the method for a virtual reality-based visual field inspection according to an embodiment performs a visual field inspection by outputting while continuously controlling the brightness of an indicator and enabling an examinee to perform inputting when outputting an indicator with brightness that the examinee can recognized, so there is an advantage that a visual field inspection can be performed within time considerably reduced in comparison to the visual field inspection of the related art.

The method for a virtual reality-based visual field inspection according to an embodiment can further improve the accuracy of a visual field inspection by calculating a visual field inspection result in consideration of the reaction speed of an examinee.

Further, the method for a virtual reality-based visual field inspection according to an embodiment can enable an examiner to quickly and accurately perform a visual field inspection by providing in real time the information related to the visual field inspection process of an examinee and an input/output interface for an examiner according to the visual field inspection progress to the examiner.

Further, the method for a virtual reality-based visual field inspection according to an embodiment uses the head-mounted display 100 relatively inexpensive in comparison to the existing eye examination equipment and can perform several ophthalmic examinations through the head-mounted display 100, so the cost for an ophthalmic examination can be reduced.

Further, the method for a virtual reality-based visual field inspection according to an embodiment performs a visual field inspection of an examinee using the head-mounted display 100, so a visual field inspection can be performed on an examinee in a more comfortable environment.

Further, the method for a virtual reality-based visual field inspection according to an embodiment performs a visual field inspection through a visual field inspection service provider server, so the data processing speed is improved, whereby it is possible to quickly perform an inspection and update and provide the newest visual field inspection method.

Method for Virtual Reality-Based Visual Field Inspection of System for Virtual Reality-Based Visual Field Inspection Hereafter, a process in which an examiner and an examinee efficiently performs a visual field inspection through data exchange of the ophthalmic examination console device and the head-mounted display 100 is described in more detail.

Hereafter, a process of providing an ophthalmic examination method using virtual reality is described with reference to FIGS. 10 to 17. It is exemplified herein that the processor 360 directly controls external devices and analyzes data received from the external device, thereby providing the ophthalmic examination function. However, as described above, it may be possible to consider an embodiment in which the ophthalmic examination service provider server 700 analyzes data for various ophthalmic examinations or inspection data or calculates ophthalmic examination result values through analysis.

First, the computing device 300 activated by input from a user can check connection between the head-mounted display 100 and the display device 500 (S101).

In detail, when the computing device 300 is activated and an ophthalmic examination program is executed, the computing device 300 can check whether there is connection or not by transmitting a connection check signal to the head-mounted display 100 and the display device 500 that are connected in advance/newly.

In an embodiment, when the display device 500 is powered, the computing device 300 connected with the display device 500 can output a graphic image related to start of an ophthalmic examination program by transmitting a driving signal (S301).

Further, the computing device 300 can activate the head-mounted display 100 by transmitting a driving signal to the head-mounted display 100 registered in advance through wire/wireless communication (S201).

Further, the computing device 300 can check whether there is connection or not by receiving a feedback signal for the connection check signal (S102).

The computing device 300 for checking connection can provide an ophthalmic examination setting interface for setting an ophthalmic examination for an examiner in the early stage (S103).

First, the computing device 300 can output a graphic image related to the ophthalmic examination setting to an examiner through the display device 500 and can progress an examination by receiving input from the examiner through the input device 400 or touch (S302).

In detail, referring to FIG. 11, the main image of the ophthalmic examination setting interface can show examinee information input 41, calibration 42 with the head-mounted display 100, and an icon for performing at least one or more ophthalmic examinations.

The examinee information input icon, which is a setting window execution icon for an examiner to input the information of an examinee to be examined, may enable an examiner to input personal information such as the name, age, and eyeball state of the examinee such that inspection data or result values are matched with the personal information of the examinee to be able to be discriminated from other examination values.

Further, an icon for calibration with the head-mounted display can execute work for focusing of an examinee wearing the head-mounted display.

In detail, when the head-mounted display 100 is calibrated, an image showing that calibration is being performed to the examiner may be displayed on the display device 500, as shown in FIG. 12.

It is preferable that the examiner does not control the head-mounted display during calibration, so as shown in FIG. 12, it would be preferable to prevent the display device 500 from performing an ophthalmic examination.

Further, on the ophthalmic examination, pointers can be displayed with left eye and right eye areas separated and a text inducing looking at the displayed pointer can be displayed, as shown in FIG. 13. It is preferable that the pointers are green that less stimulates the eyeballs and can stimulate the optic nerves.

When calibration is finished, the computing device 300 can sense input from a user and progress a visual field inspection in accordance with the sensed input (S104).

In detail, the computing device 300 can sense selective input for the visual field inspection of a plurality of ophthalmic examinations through a direct touch on the input device 400 or the display device 500.

In an embodiment, the ophthalmic examinations that are provided by the computing device may include one or more of a visual field test, a stabismusangle test, a extraocular muscle test, a stereopsia test, and/or a Lancaster test. The tests are currently performed by doctors manually directly putting examination tools close to the eyeballs of an examinee. Such manual tests are performed on the basis of the subjective determinations of doctors and the feeling of examinees, so they are incorrect, take long time, and cause inconvenient to the examiners and examinees.

Returning to description, referring to FIG. 14 an examiner can perform a visual field inspection function by touching a visual field inspection icon 43 of icons for at least one or more of a visual field test, a stabismusangle test, a extraocular muscle test, a stereopsia test, or a Lancaster test.

In an embodiment, when the visual field inspection icon 43 is selected, the computing device 300 can receive data for the selected visual field inspection from the ophthalmic examination service provider server 700. That is, the computing device 300 can receive newest updated data about the visual field inspection in real time and provide the data to the examinee and the examiner.

Further, the ophthalmic examination service provider server 700 can request the cost for providing a service later by counting the number of times of ophthalmic examinations.

In another embodiment, the computing device 300 can progress a visual field inspection by loading the data for the visual field inspection from the memory 330.

Further, the virtual reality-based visual field inspection can be performed by providing a visual field inspection virtual reality image to an examinee through the head-mounted display and obtaining reaction information of the examinee to the provided visual field inspection virtual reality image.

In detail, in order to perform a visual field inspection, the computing device 300 can control the head-mounted display to output a virtual reality image related to the visual field inspection by transmitting a virtual reality image about the visual field inspection to the head-mounted display.

The head-mounted display receiving the virtual reality image can output a virtual reality image related to the visual field inspection (S202).

Since the head-mounted display includes the display unit 270 separated into a left eye area and the right eye area, the head-mounted display can output different virtual reality images to the left eye area and the right eye area.

For example, referring to FIG. 15, the head-mounted display may output a background including a background image BA and a focus point FP, and an indicator P on the display unit 270 of the left eye area LA, and the background may be output on the display unit 270 of the right eye area RA.

Further, in an embodiment, a visual field inspection may be performed by determining whether an examinee recognizes an indicator P in a specific area around a focus point FP that is the gaze of the examinee looking at the focus point FP while the examinee continuously looks at the focus point FP output on the head-mounted display.

The detailed visual field inspection process is the same as the visual field inspection of the head-mounted display described above, so the detailed description is omitted.

Further, the head-mounted display outputting the virtual reality image can create measurement data by measuring an eyeball reaction to the visual field inspection virtual reality image through the eye examination unit 250 (S203).

Further, the head-mounted display can check whether or not recognition of an examinee based on the focus point FP by sensing user input through the input unit or the user input unit 120 connected to the head-mounted display, and can connect and include the checked input and the point in time of input in the measurement data.

Further, various virtual reality images for performing a visual field inspection are sequentially transmitted to the head-mounted display through the computing device 300, and the head-mounted display can obtain and transmit measurement data of the examinee based on the sequentially transmitted virtual reality images to the computing device 300 while outputting the virtual reality images.

Further, while an examination is performed in the head-mounted display, the computing device 300 can control the display device 500 to output a visual field inspection progress image for the examiner.

In detail, the display device 500 can be controlled by the computing device 300 to display a visual field inspection progress image for an examiner that enables an examiner to check the process of a visual field inspection through the head-mounted display (S303).

To this end, the computing device 300 can transmit the visual field inspection progress image for an examiner, which includes a visual field inspection image, measurement data, measurement data analysis values, etc. obtained by converting virtual reality images for a visual field inspection output from the head-mounted display in real time into 2D graphic images, to the display device 500.

Meanwhile, the computing device 300 receiving the measurement data can create visual field inspection progress information on the basis of the received measurement data (S105).

In detail, referring to FIG. 16, the computing device 300 can create visual field inspection progress information including at least one or more items of information of personal information 61 of an examinee, a visual field inspection virtual reality image 62 converted to be suitable for the display device 500 from a virtual reality image output from the head-mounted display, measurement data 64 sensed by the head-mounted display, a visual field inspection result value 65 according to the measurement data 64, calibration data, and other information 65.

The computing device 300 can transmit a visual field inspection progress image for an examiner based on the created visual field inspection progress information to the display device 500.

The display device 500 can display and provide the visual field inspection progress image for an examiner based on the visual field inspection progress information received from the computing device 300 to an examiner (S304).

These items of information can be output through real-time analysis of the computing device 300 and the visual field inspection service provider server 700 may perform some of the analysis.

In detail, it is possible to whether a correct examinee is taking an examination through the person information 61 of an examinee.

Further, the display device 500 can output in real time the inspection data 64 of the examinee for the visual field inspection virtual reality image such that the examiner checks in real time the state of the examinee and performs the inspection in the right way.

For example, in the visual field inspection progress image, an eyeball position value or/and a pupil tracking value that are calibration data of eyeballs may be calculated and displayed as a number.

Accordingly, the display device 500 can quickly monitor the visual field inspection progress situation by displaying reaction information of the examine to the visual field inspection virtual reality image as numbers.

Further, the display device 500 can include the visual field inspection result value 65 according to the real-time measurement data 64 into the visual field inspection providing image.

Further, the display device 500 can provide the visual field inspection result value 65 to the examiner such that the examiner intuitionally checks the eyeball state of the examinee.

Further, the display device 500 can provide an interface such that the examiner can control the visual field inspection on the basis of the visual field inspection result value 65.

In detail, the display device 500 can enable the examiner to freely select the display position of an indicator P output on the head-mounted display.

Further, the display device 500 can receive input about the display position of the indicator P freely selected by the examiner on an image showing the visual field inspection result value 65.

As an embodiment, the examiner, first, can determine the position of an indicator P for an effective visual field inspection on the basis of the visual field inspection result value 65 output from the display device 500.

In more detail, the examiner checking the recognition indicator P shown in the visual field inspection result value 65 can determine that indicators P pertaining to an are closer to the focus point FP than the checked recognition indicator P pertains to a recognizable visual field area.

Further, the examiner can perform a visual field inspection for the other indicators P excepting the indicators P determined as pertaining to the recognizable visual field area. To this end, the examiner can perform input for the indicator P determined as the position of an indicator that is the most effective in the visual field inspection of the other indicators P, and can perform more quickly and effectively the visual field inspection.

The display device 500 can provide an interface that can receive input for the indicator P determined as the position of an indicator that is the most effective on the basis of the visual field inspection result value 65 from the examiner.

Accordingly, the display device 500 can assist the examiner to more quickly and accurately perform the virtual reality-based visual field inspection.

Further, the display device 500 can display eyeball state information according to the measurement data 64 measured up to now, and the examiner may finis the inspection by more quickly checking the inspection progress state through the eyeball state information.

The eyeball state information may be directly analyzed and derived by the computing device 300.

That is, the display device 500 outputs the eyeball state information together with eyeball state information showing the process of calculating the result value 65 such that the examiner can more clearly check the inspection result.

Further, the display device 500 can display the visual field inspection virtual reality image 62 converted to be suitable for the display device 500 from the virtual reality image output on the head-mounted display.

That is, visual field inspection virtual reality image output from the display device 500 may be a virtual reality image obtained by converting the virtual reality image output from the head-mounted display into a 2D graphic image, and the examiner can check whether a visual field inspection is performed in the right way through the 2D graphic image.

Further, depending on embodiments, the display device 500 can display a real-time eyeball image directly taken from an eyeball reaction of the examinee.

In detail, the display device 500 may include an image obtained by taking in real time the balls of the examinee in the visual field inspection progress image, and may further include the pupil tracking information, the eyeball position information, and/or the eyeball position information, etc. of the examinee while the visual field inspection is performed in the visual field inspection progress image.

Further, the display device 500 may display and collectively output multiple information including at least one or more items of the pupil tracking information, the eyeball position information, and/or the eyeball position information of the examinee in the real-time eyeball image of the examinee.

Accordingly, the display device 500 can provide the multiple image to be easily checked by the examiner at a glance, and can improve the quality of the visual field inspection.

Further, the display device 500 can assist the examiner to be able to determine whether the examiner looks at the focus point which has a great influence on the reliability of the visual field inspection result.

When a visual field inspection is performed, it is very important for the accuracy of the inspection result that the examinee keeps looking at the focus point provided such that the examinee keeps locking at the focus point while the visual field inspection is performed. It was difficult for an examiner to check whether an examinee looks at a focus point using the existing eye examination equipment, but it is possible to easily check whether an examinee looks at a focus point in the digital visual field inspection based on virtual reality.

Returning to the description, the display device 500 can display and provide the pupil tracking information, eyeball position information, and/or eyeball position information, etc. of the examinee together with the real-time eyeball image to the examiner.

Accordingly, the display device 500 can provide whether the examinee taking an visual field inspection accurately keeps looking at the focus point FP output from the head-mounted display.

That is, the display device 500 can sense and provide a looking reaction of the examiner for the focus point, which is difficult to check through the existing eye examination equipment, to the examiner, and enables more derivation of more accurate visual field inspection result.

Meanwhile, referring to FIG. 16, in the visual field inspection progress image for an examiner, a control icon that can control in real time the virtual reality image output from the head-mounted display may be further included.

That is, when an examiner inputs a signal for controlling a head-mounted display image through the control icon included in the visual field inspection progress image for an examiner, the computing device 300 can change the virtual reality image output from the head-mounted display in accordance with user input by transmitted in a virtual reality image reflecting the signal to the head-mounted display (S106 and S204).

In detail, the control icon may include an eyeball selection icon 71 that can determine an eyeball on which a visual field inspection is performed.

In detail, the eyeball selection icon 71 is an icon for selecting whether the eyeball to be examined is the left eye or the right eye, and when the left eye icon is selected, a virtual reality image is output in the left eye area LA of the head-mounted display, so a visual field inspection can be performed on the left eye of the examinee.

Further, the control icon may include an icon for determining the color of a virtual reality image that is output from the head-mounted display.

In detail, the control icon may include at least two or more color change icons that can change the color of a virtual reality image. The color change icon can improve the examination environment of examinees with color blindness and color weakness.

Further, the control icon may include an adjustment bar 73 that can adjust the depth of a virtual reality image. The adjustment bar 73 can help progress various visual field inspections by changing the position of a virtual reality image.

Further, the control icon may include a reset button that stops or starts a progress of a visual field inspection or initializes the entire visual field inspection.

The progress-related execution icon 74 can help the examiner to quickly stops and restart an examination on the basis of the measurement data 64 and the 2D examination images that are output in real time when it is determined that the examination is wrong or the examinee has a problem.

Finally, the control icon may further include a button for storing the examination result and printing offline output data.

As a result, the computing device 300 according to an embodiment output visual field inspection progress information by controlling the display device 500, thereby assisting an examiner to check the examination progress process. Further, the computing device provides an interface for controlling real time a virtual reality image output from the head-mounted display in this case, whereby an examination can be more quickly and accurately performed.

Finally, the computing device 300 can create visual field inspection result information on the basis of the visual field inspection progress information created on the basis of the inspection data 64 (S107).

In detail, the computing device 300 can create information about the visual field inspection result of an examinee by on the basis of the visual field inspection progress information created on the basis of the measurement data 64 matched with the sequentially output virtual reality images.

In an embodiment, the computing device 300 transmits in real time the measurement data 64 matched to the virtual reality images to the visual field inspection service provider server 700 and the visual field inspection service provider server 700 receiving the measurement data calculates visual field inspection result information of the examinee by analyzing the measurement data 64 and transmits the calculated result to the computing device 300, whereby it is possible to acquire visual field inspection result information.

In the process of calculating visual field inspection result information, the information about values obtained by tracking the positions of the pupils from an eyeball image, the position information of the eyeballs, the information obtained through image-deep learning of eyeball reaction, sensed measurement data 64, eyeball state information according to the measurement data 64, and/or other information 65 may be included, and the visual field inspection result information is calculated in accordance with these items of objective information, so the visual field inspection result information can be accurate and precise.

Finally, the computing device 300 can transmit the acquired visual field inspection result information to the display device 500 and control the display device 500 to output the received visual field inspection result information (S305).

In detail, referring to FIG. 17, the computing device 300 may include personal information 81 of an examinee, a visual field inspection result value 82 based on the measurement data 64, and/or eyeball state information 83 based on the visual field inspection result value 82, etc. in the visual field inspection result information.

The visual field inspection result value 82 may show the consequent result information of the virtual reality-based visual field inspection created on the basis of the visual field inspection virtual reality image 62, the measurement data 64, the other information 65, and/or measurement data analysis information through deep learning, etc.

Further, the eyeball state information 83 based on the visual field inspection result value 82 may show the eyeball state using an eyeball image, to which the visual field inspection result is applied, such that the user can intuitionally know the eyeball information of the examinee based on a visual field inspection.

AS described above, the method for virtual reality-based visual field inspection according to an embodiment performs a digital visual field inspection using VR, so it is possible to acquire a visual field inspection result of an examinee quickly and accurately without using specific eye examination equipment.

Embodiments of the present disclosure described above may be implemented in the type of program commands the can be executed through various computer components, and may be recorded on a computer-readable recording medium. The computer-readable recording medium may include program commands, data files, and data structures individually or in combinations thereof. The program commands that are recorded on a computer-readable recording medium may be those specifically designed and configured for the present invention or may be those available and known to those engaged in computer software in the art. The computer-readable recording medium includes magnetic media such as hard disks, floppy disks, and magnetic media such as a magnetic tape, optical media such as CD-ROMs and DVDs, magneto-optical media such as floptical disks, and hardware devices specifically configured to store and execute program commands, such as ROM, RAM, and flash memory. The program commands include not only machine language codes compiled by a compiler, but also high-level language code that can be executed by a computer using an interpreter etc. A hardware device may be changed into one or more software module to perform the processes according to the present disclosure, and vice versa.

Specific execution described herein is embodiments and does not limit the present disclosure in any way. For briefness of the specification, electronic components, control systems, and software of the related art, and other functions of the system may not be described. Furthermore, wire connection and connecting members of components shown in the figures are examples of functional connection and/or physical or circuit connections, and in actual devices, they may be replaceable or may be shown as various additional functional connection, physical connection, or circuit connection. Unless stated in detail such as "necessary" and "important", they may not be necessary component for the present disclosure.

Although exemplary embodiments of the present disclosure were described above, it should be understood that the present disclosure may be changed and modified in various ways by those skilled in the art without departing from the spirit and scope of the present disclosure described in the following claims. Therefore, the technical scope of the present disclosure is not limited to the exemplary embodiments described herein, but should be determined by claims.

INDUSTRIAL AVAILABILITY

The method and system for virtual reality-based visual field inspection of the present disclosure relate to medical examination equipment for performing a visual field inspection on the eyeballs of an examinee using virtual reality, so the present disclosure has industrial applicability.

What is claimed is:

1. A method for virtual reality-based visual field inspection in which a processor of a head-mounted display performs a visual field inspection, the method comprising:
   outputting a background including a background image and a focus point image;
   outputting an indicator in the background;
   sensing user input from an examinee according to output of the indicator,
   wherein the outputting of an indicator in the background includes determining a position where the indicator will be output in the background, outputting the indicator with predetermined brightness at the determined position, and continuously increasing the brightness of the output indicator,
   measuring a reaction speed of the examinee,
   wherein the measuring of the reaction speed of the examinee includes calculating the reaction speed by outputting an indicator for measuring the reaction speed with predetermined brightness at a predetermined position in the background, and then sensing user input; and
   acquiring a visual field inspection result on the basis of the reaction speed, an output position of the indicator, a point in time of outputting the indicator, and a point in time of the user input.

2. The method of claim 1, wherein the continuously increasing of the brightness of the output indicator includes increasing the brightness of the indicator by controlling transparency of a pixel showing the indicator.

3. The method of claim 1, wherein the increasing of the brightness of the indicator by controlling transparency of a pixel showing the indicator includes:
   outputting the indicator while setting the transparency of the pixel showing the indicator at the point in time of outputting as a first value; and
   gradually increasing the brightness of the indicator by uniformly increasing the transparency of the pixel from the first value as time passes.

4. The method of claim 1, the continuously increasing of the brightness of the output indicator includes:
   increasing the brightness of the indicator at a first speed for a first period after the point in time of outputting; and
   increasing the brightness of the indictor at a second speed smaller than the first speed for a second period after the first period.

5. The method of claim 1, wherein the outputting of an indicator in the background further includes:
   stooping output of the output indicator, and determining a next position where an indicator is output in the background, when the user input is sensed while the brightness of the indicator is increased.

6. The method of claim 1, wherein the outputting of a background including a background image and a focus point image includes displaying a first background and the indicator in a left eye area of a display unit and simultaneously displaying only a second background that is the same as the first background in a right eye image of the display unit.

7. The method of claim 1, wherein the calculating of the reaction speed by outputting an indicator for measuring the reaction speed with predetermined brightness at a predetermined position in the background, and then sensing user input includes:
   determining one position of a first position at the left upper end, a second position at the right upper end, a third position at the left lower end, and a fourth position at the right lower end with respect to the focus point image that is an origin; and
   outputting the indicator for measurement at the determined position.

8. The method of claim 1, wherein the calculating of the reaction speed by outputting an indicator for measuring the reaction speed with predetermined brightness at a predetermined position in the background, and then sensing user input includes:
   sequentially outputting the indicator for measurement at a plurality of positions of a first position at the left upper end, a second position at the right upper end, a third position at the left lower end, and a fourth position at the right lower end with respect to the focus point image that is an origin; and
   determining the reaction speed of the user on the basis of a time difference between the point in time of outputting a plurality of the indicators for measurement and the point in tome of user input.

9. The method of claim 1, wherein acquiring of a visual field inspection result on the basis of the reaction speed, an output position of the indicator, a point in time of outputting the indicator, and a point in time of the user input includes:
- calculating a light sensitivity threshold for the position of the indicator by applying the reaction speed determined at the point in time of user input; and
- acquiring a graph showing a light sensitivity threshold calculated for each display position of the indicator as visual field inspection result information.

10. A method for virtual reality-based visual field inspection in which an ophthalmic examination console device performs a visual field inspection by controlling a head-mounted display, the method comprising:
- providing an ophthalmic examination setting interface for inputting user setting for an ophthalmic examination;
- performing a visual field inspection when the visual field inspection is selected from the interface;
- controlling the head-mounted display to output a virtual reality image for the visual field inspection;
- acquiring measurement data according to the virtual reality image from the head-mounted display;
- outputting a visual field inspection progress image for an examiner for the visual field inspection by controlling a display device,
- wherein the controlling of the head-mounted display to output a virtual reality image for the visual field inspection includes:
  - outputting a background including a background image and a focus point image; and
  - outputting an indicator in the background, and
  - the outputting of the indicator in the background includes:
    - determining a position where an indicator will be output in the background;
    - outputting an indicator with predetermined brightness at the determined position; and
    - continuously increasing the brightness of the output indicator;
- measuring a reaction speed of the examinee,
- wherein the measuring of the reaction speed of the examinee includes calculating the reaction speed by outputting an indicator for measuring the reaction speed with predetermined brightness at a predetermined position in the background, and then sensing user input; and
- acquiring a visual field inspection result on the basis of the reaction speed, an output position of the indicator, a point in time of outputting the indicator, and a point in time of the user input.

11. The method of claim 10, wherein the outputting of a visual field inspection progress image for an examiner by controlling a display device includes outputting progress information of a visual field inspection that is progressed in real time, and
the visual field inspection progress information includes at least one or more of personal information of the examinee, a visual field inspection VR image, the inspection data, analysis values according to the inspection data, and a real-time visual field inspection result value.

12. The method of claim 11, wherein the visual field inspection VR image includes a graphic image obtained by converting a 3D VR image output from the head-mounted display into 2D.

13. The method of claim 12, wherein the outputting of a visual field inspection progress image for an examiner by controlling a display device further includes:
- outputting the graphic image obtained by converting a 3D VR image for a visual field inspection into 2D on the display device; and
- providing an examiner with an interface controlling the 3D VR image of the head-mounted display during the visual field inspection.

14. The method of claim 13, wherein the providing of an examiner with an interface controlling the 3D VR image of the head-mounted display during the visual field inspection includes changing at least one or more of a shape, a size, brightness, illuminance, chroma, luminosity, depth, or an output position of the 3D VR image.

15. The method of claim 14, wherein the changing of at least one or more of a shape, a size, brightness, illuminance, chroma, luminosity, depth, or an output position of the 3D VR image includes:
- changing a background of the VR image; and
- changing an indicator of the VR image.

16. The method of claim 10, further comprising:
- acquiring visual field inspection result information on the basis of the inspection data matched to a VR image for the visual field inspection; and
- outputting the acquired visual field inspection result information.

17. The method of claim 16, wherein the acquiring of visual field inspection result information on the basis of the inspection data includes:
- transmitting the inspection data to a visual field inspection service provider server; and
- receiving visual field inspection result information based on the inspection data from the visual field inspection service provider server.

* * * * *